US011078153B2

(12) United States Patent
Silverman

(10) Patent No.: US 11,078,153 B2
(45) Date of Patent: Aug. 3, 2021

(54) 2-DIFLUORO SUBSTITUTED 4-AMINOCYCLOPENTANECARBOXYLIC ACIDS AS INHIBITORS OF GAMMA-AMINOBUTYRIC ACID AMINOTRANSFERASE AND HUMAN ORNITHINE AMINOTRANSFERASE

(71) Applicant: Northwestern University, Evanston, IL (US)

(72) Inventor: Richard B. Silverman, Winnetka, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 16/839,441

(22) Filed: Apr. 3, 2020

(65) Prior Publication Data
US 2020/0317606 A1    Oct. 8, 2020

Related U.S. Application Data

(60) Provisional application No. 62/828,685, filed on Apr. 3, 2019.

(51) Int. Cl.
*C07C 229/48*    (2006.01)

(52) U.S. Cl.
CPC .................. *C07C 229/48* (2013.01)

(58) Field of Classification Search
CPC .................................................. C07C 229/48
USPC ........................................................ 514/561
See application file for complete search history.

(56) References Cited

U.S. PATENT DOCUMENTS

| 6,794,413 | B1 | 9/2004 | Silverman |
| 7,381,748 | B1 | 6/2008 | Silverman |
| 8,211,865 | B2 | 7/2012 | Ilan |
| 8,686,041 | B2 | 4/2014 | Ilan |
| 9,603,820 | B2 * | 3/2017 | Silverman ............... A61P 35/00 |
| 9,670,141 | B2 | 6/2017 | Silverman |
| 10,632,088 | B2 | 4/2020 | Silverman |
| 10,822,301 | B2 | 11/2020 | Silverman |

(Continued)

FOREIGN PATENT DOCUMENTS

WO    WO-2016145082 A1 *    9/2016    .............. A61P 25/00

OTHER PUBLICATIONS

FDA. Sabril (vigabatrin) Postmarket Drug Safety Information for Patients and Providers page. Last updated Jun. 22, 2016. Version accessed Feb. 7, 2019. Available online at http://web.archive.org/web/20190207174554/https://www.fda.gov/Drugs/DrugSafety/PostmarketDrugSafetyInformationforPatientsandProviders/ucm507990.htm.

(Continued)

*Primary Examiner* — Deborah D Carr
(74) *Attorney, Agent, or Firm* — Quarles & Brady LLP; M McBride

(57) ABSTRACT

Disclosed are enantiomerically pure cyclopentane-based compounds that are prepared by a multiple-step synthesis process. The disclosed compounds have been designed to inhibit gamma-aminobutyric acid-amino transferase (GABA-AT) activity and ornithine aminotransferase (OAT) activity. Some of the enantiomerically pure compounds inhibit OAT activity more potently than the racemic compound. The disclosed compounds may be used to selectively inhibit OAT activity, for example, to treat hepatocellular carcinoma and/or used to selected inhibit GABA-AT activity, for example, to treat neurological diseases and disorders.

7 Claims, 5 Drawing Sheets

(56) References Cited

U.S. PATENT DOCUMENTS

| | | |
|---|---|---|
| 2012/0245380 A1 | 9/2012 | Ilan |
| 2013/0041028 A1 | 2/2013 | Silverman |
| 2014/0256958 A1 | 9/2014 | Silverman |
| 2015/0196522 A1 | 7/2015 | Silverman |
| 2017/0101364 A1 | 4/2017 | Silverman |
| 2017/0239202 A1 | 8/2017 | Silverman |
| 2018/0098952 A1 | 4/2018 | Silverman |
| 2018/0271816 A1 | 9/2018 | Silverman |
| 2019/0256489 A1 | 8/2019 | Silverman |
| 2019/0315677 A1 | 10/2019 | Silverman |
| 2019/0359555 A1 | 11/2019 | Silverman |
| 2020/0281880 A1 | 9/2020 | Silverman |
| 2020/0317606 A1 | 10/2020 | Silverman |

OTHER PUBLICATIONS

International Searching Authority. International Search Report and Written Opinion for application PCT/US2020/026554, dated Jun. 11, 2020.

Juncosa, J. L, et al. "Design and Mechanism of (S)-3-Amino-4-(Difluoromethylenyl)Cyclopent-1-Ene-1-Carboxylic Acid, a Highly Potent Gamma-Aminobutyric Acid Aminotransferase Inactivator for the Treatment of Addiction." J Am Chem Soc 2018, 140, 2151-2164. PMC5812813.

Pan, Y. et al. (1S, 3S)-3-Amino-4-difluoromethylenyl-1-cyclopentanoic Acid (CPP-115), a Potent ?-Aminobutyric Acid Aminotransferase Inactivator for the Treatment of Cocaine Addiction. J. Med. Chem. 2012. 55, 357-366.

Shen et al. (1998), "Crystal structure of human recombinant ornithine aminotransferase," J. Mol. Biol. 277 (1):81-102.

Shields, D. Child Neurology Foundation. Infantile Spasms webpage. Version available Mar. 31, 2019. Accessed online at http://web.archive.org/web/20190331094206/https://www.childneurologyfoundation.org/disorders/infantile-spasms/.

Silverman, R. B. "[10] Mechanism-Based Enzyme Inactivators." Methods in enzymology 1995, 249, 240-283.

Silverman, R. B. Design and Mechanism of GABA Aminotransferase Inactivators. Treatments for Epilepsies and Addictions. Chem. Rev. 2018. 118, 4037-4070.

Storici et al. (2018), "Design and Mechanism of (S)-3-Amino-4-(difluoromethylenyl)cyclopent-1-ene-1-carboxylic Acid, a Highly Potent ?-Aminobutyric Acid Aminotransferase Inactivator for the Treatment of Addiction," J. Am. Chem. Soc. 140 (6)2151-2164.

Strelow, J. M. A Perspective on the Kinetics of Covalent and Irreversible Inhibition. SLAS Discovery. 2017. 22, 3-20.

Zigmond, E. et al. Suppression of Hepatocellular Carcinoma by Inhibition of Overexpressed Ornithine Aminotransferase. ACS Med. Chem. Lett. 2015. 6, 840-844.

* cited by examiner

2-DIFLUORO SUBSTITUTED 4-AMINOCYCLOPENTANECARBOXYLIC ACIDS AS INHIBITORS OF GAMMA-AMINOBUTYRIC ACID AMINOTRANSFERASE AND HUMAN ORNITHINE AMINOTRANSFERASE

CROSS-REFERENCE TO RELATED PATENT APPLICATIONS

The present application claims the benefit of priority under 35 U.S.C. § 119(e) to U.S. Provisional Application No. 62/828,685, filed on Apr. 3, 2019, the content of which is incorporated herein by reference in its entirety.

STATEMENT REGARDING FEDERALLY SPONSORED RESEARCH OR DEVELOPMENT

This invention was made with government support under DA030604 and NS015703 awarded by the National Institutes of Health. The government has certain rights in the invention.

BACKGROUND

The invention relates to new compounds and compositions. In particular, the invention relates to new compounds, compositions comprising the new compounds, and methods of using the compounds and compositions for treating diseases and disorders, including diseases and disorders that are associated with γ-aminobutyric acid aminotransferase (GABA-AT) activity and/or ornithine aminotransferase (OAT) activity.

Gamma-Aminobutyric acid (GABA) is the major inhibitory neurotransmitter in the central nervous system. GABA is produced in presynaptic GABAergic neurons from L-glutamate by the enzyme glutamic acid decarboxylase (GAD). GABA is then released by the presynaptic GABAergic neurons into the synapse and transported to glial cells. In glial cells, the enzyme GABA aminotransferase (GABA-AT), a pyridoxal 5'-phosphate (PLP)-dependent enzyme, degrades GABA to succinic semialdehyde (SSA), which is further oxidized to succinate and enters the Krebs cycle. GABA-AT also converts α-ketoglutarate from the Krebs cycle to L-glutamate. Because there is no GAD in glial cells, this newly formed L-glutamate is not converted to GABA. It is instead converted to L-glutamine by glutamine synthetase, which is then released from glial cells into the synapse and transported back to GABAergic neurons to complete the metabolic cycle of L-glutamate.

After GABA is released from presynaptic GABAergic neurons, GABA binds to chloride-selective ion channel receptors including (GABAA and GABAc) and to G-protein coupled receptors that are linked to potassium-selective ion channels including (GABAB). Binding of GABA to these receptors causes the receptors to selectively conduct their respective ions and hyperpolarize the postsynaptic membrane, thereby controlling neuronal activity downwardly. Low levels of GABA are linked to many neurological disorders, including epilepsy, Parkinson's disease, Alzheimer's disease, Huntington's disease, and cocaine addiction.

GABAergic drugs are those that improve secretion or transmission of GABA. These drugs as a family have been used to treat a wide variety of nervous system disorders including fibromyalgia, neuropathy, migraines related to epilepsy, restless leg syndrome, and post traumaticpost-traumatic stress disorder. GABAergic drugs include GABAA and GABAB receptor ligands, GABA reuptake inhibitors, GABA aminotransferase inhibitors, GABA analogs, or molecules containing GABA itself.

In 1998, a novel strategy was developed for the treatment of cocaine addiction by inhibiting the activity of gamma-aminobutyric acid aminotransferase (GABA-AT). GABA-AT inhibition raises GABA levels, which antagonizes the rapid release of dopamine in the nucleus accumbens (NAcc), a neurochemical response to cocaine and other drugs of abuse. Following this strategy, vigabatrin was developed as an inactivor of GABA-AT and currently is the only FDA-approved inactivator of GABA-AT.

Vigabatrin is currently used as an antiepilepsy drug, and vigabatrin has been successful in the treatment of addiction in animal models for cocaine, nicotine, methamphetamine, heroin, and alcohol. Vigabatrin also was effective in the treatment of cocaine addiction in humans, with up to 28% of patients achieving abstinence in a 9-week double-blind trial. The potential of vigabatrin for general therapeutic use, however, may be problematic. In order to treat epilepsy, a large dose of vigabatrin (~1-3 g) needs to be taken daily, and there are many serious side effects that arise from its usage. Permanent vision loss has been reported to arise from its long-term administration in 25-40% of epilepsy patients resulting from the damage of the retinal nerve fiber layer. Negative psychological effects also have been observed in patients treated with vigabatrin. As a result, the search for an alternative to vigabatrin in the treatment of epilepsy has been an ongoing concern in the art.

One strategy for new inhibitors of GABA-AT relates to the design of mechanism-based inactivators, in particular, the design of unreactive compounds that require GABA-AT catalysis to convert the unreactive compounds into a species that inactivates the enzyme. Because these molecules are not initially reactive, but require the catalytic activity of GABA-AT to become activated and form covalent bonds, indiscriminate reactions with off-target proteins, leading to undesired side effects, should be greatly reduced. Even at lower dosages, these inactivators should be able to achieve the desired pharmacologic effects with enhanced potency and selectivity than conventional inhibitors.

Another pyridoxal 5'-phosphate (PLP)-dependent enzyme belonging to the same evolutionary subgroup as GABA-AT is the enzyme ornithine aminotransferase (OAT). These two enzymes share a high structural homology and, like all aminotransferases, also have very similar catalytic mechanisms. OAT is expressed in many tissues, including liver, kidney, small intestine, brain, and eye and catalyzes the reversible conversion of ornithine and α-ketoglutarate to L-glutamate semialdehyde which cyclizes to Ai-pyrroline-5-carboxylate and L-glutamate. L-glutamate is then converted by glutamine synthetase to L-glutamine. Glutamine is the most abundant free amino acid in the body and it is essential for growth of both normal and neoplastic cells. However, tumor cells take up glutamine more efficiently than normal cells, and tumor growth is enhanced by glutamine. With respect to glutamine, cancer cells distinguish themselves from normal cells in that they have an increased requirement for glutamine to support anabolic processes that stimulate proliferation. Because of the structural similarities between OAT and GABA-AT, it has been shown that some inactivators of GABA-AT also inactivate OAT. Therefore, the compounds disclosed herein as inactivators of GABA-AT may also be used to modulate, reduce and/or inhibit OAT activity and may be useful in the treatment of malignant pathologic proliferative disorders, including but not limited to hepatocellular carcinoma (HCC).

SUMMARY

Disclosed herein are enantiomerically pure cyclopentane-based compounds that are prepared by multiple-step synthesis process. The disclosed compounds have been designed to inhibit gamma-aminobutyric acid-amino transferase (GABA-AT) activity and ornithine aminotransferase (OAT) activity. Some of the enantiomerically pure compounds inhibit OAT activity more potently than the racemic compound. The disclosed compounds may be used to selectively inhibit OAT activity, for example, to treat hepatocellular carcinoma and/or used to selected inhibit GABA-AT activity, for example, to treat neurological diseases and disorders.

DETAILED DESCRIPTION

Figure 1:
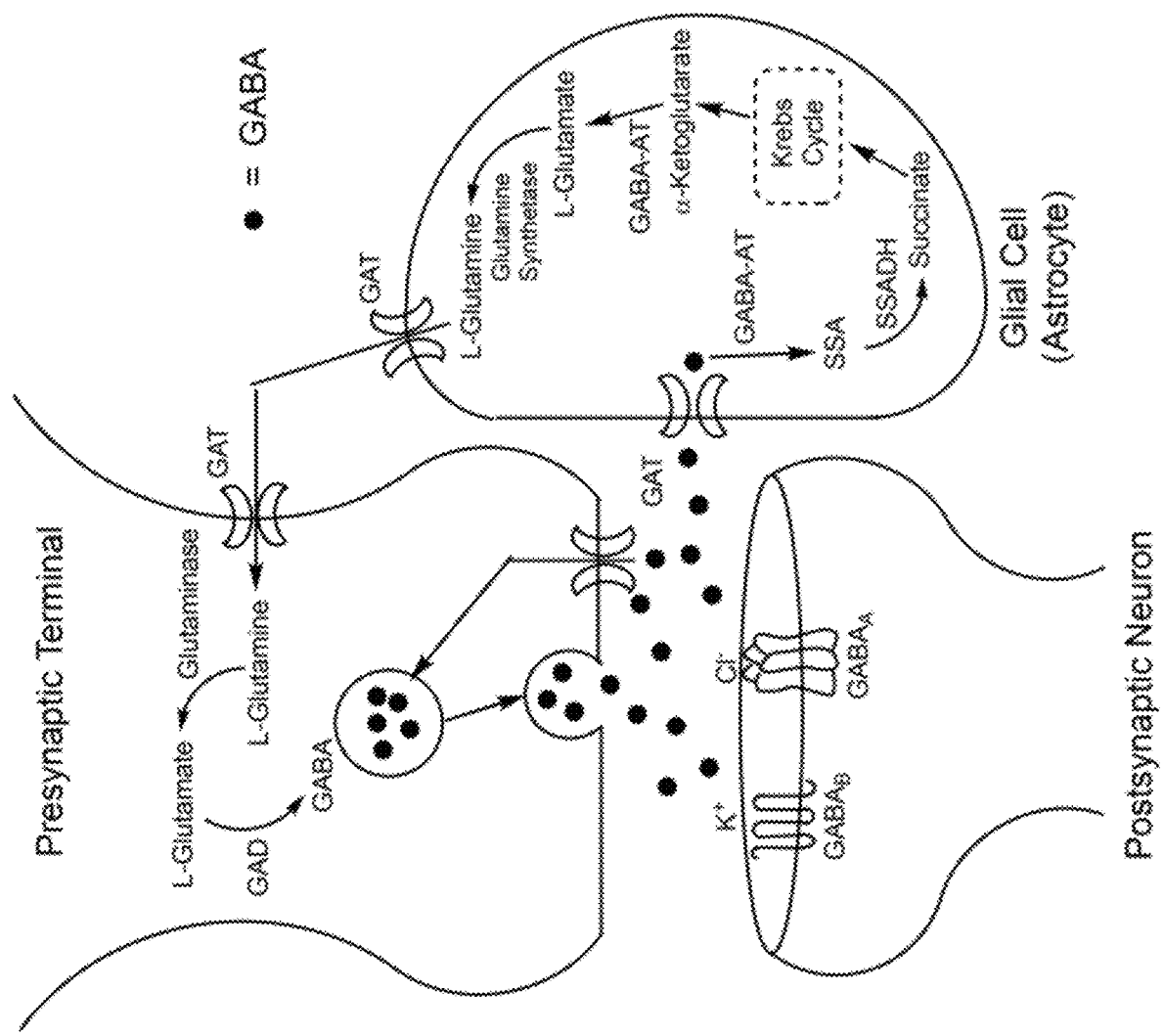
FIG. 1. Breakdown of GABA (from Silverman, R. B. Design and Mechanism of GABA Aminotransferase Inactivators. Treatments for Epilepsies and Addictions. *Chem. Rev.* 2018. 118, 4037-4070).
Figure 2:
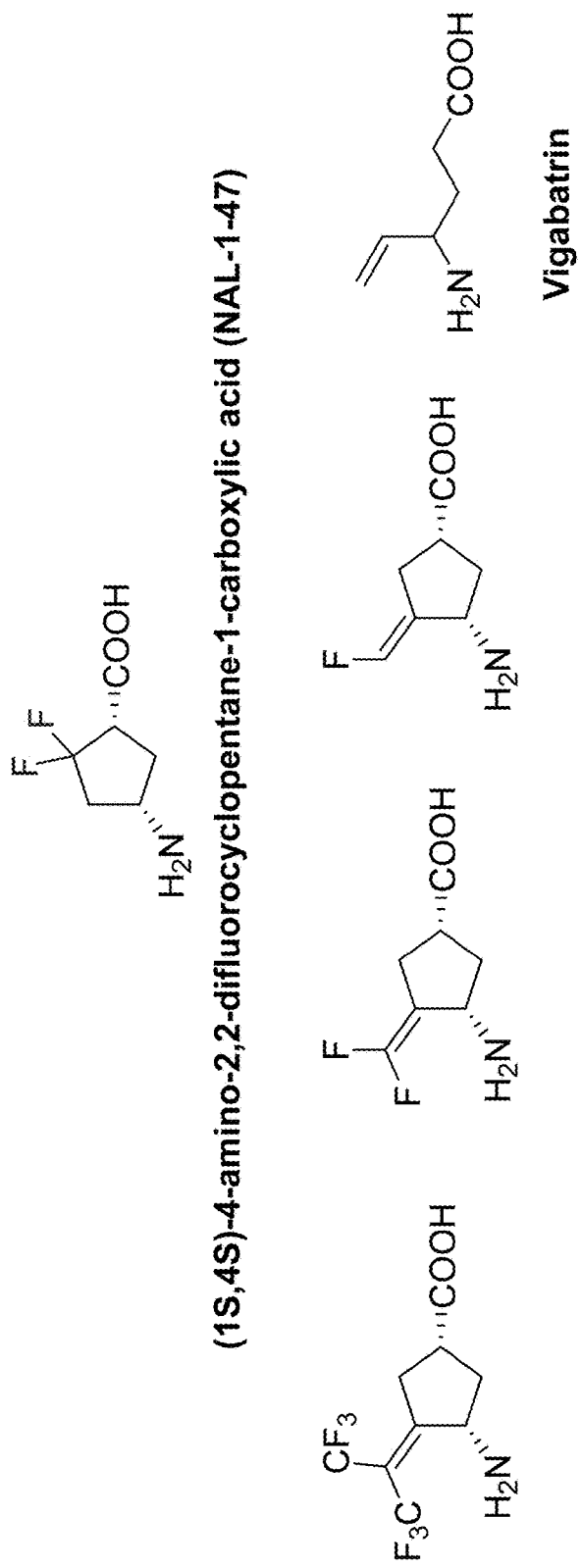
FIG. 2. The structure of new analog NAL-1-47 and known GABA-AT inhibitors (from Silverman, R. B. Design and Mechanism of GABA Aminotransferase Inactivators. Treatments for Epilepsies and Addictions. *Chem. Rev.* 2018. 118, 4037-4070).

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a therapeutic agent" should be interpreted to mean "one or more therapeutic agents." As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the phrase "effective amount" shall mean that drug dosage that provides the specific pharmacological response for which the drug is administered in a significant number of patients in need of such treatment. An effective amount of a drug that is administered to a particular patient in a particular instance will not always be effective in treating the conditions/diseases described herein, even though such dosage is deemed to be a therapeutically effective amount by those of skill in the art.

As used herein, the term "ornithine aminotransferase" (OAT) refers to an enzyme that catalyzes a reversible reaction of interconversion between ornithine and a 2-oxo acid to an L-glutamate 5-semialdehyde and an L-amino acid. (See Enzyme Commission number 2.6.1.13). In particular, OAT catalyzes a reversible reaction of interconversion between ornithine and α-ketoglutarate to 4-1-pyrroline-5-carboxylate and glutamate. Human OAT is encoded by the OAT gene located on human chromosome 10, which encodes for a protein that is approximately 46 kDa in size. Human OAT is expressed in liver and kidney but also in the brain and the retina. Human OAT is localized in mitochondria. The structure of the human OAT protein has been resolved using X-ray crystallography. (See, e.g., Shen et al. (1998), "Crystal structure of human recombinant ornithine aminotransferase," *J. Mol. Biol.* 277 (1):81-102; the content of which is incorporated herein by reference in its entirety).

As used herein, the term "gamma aminobutyric acid aminotransferase (GABA-AT) refers to an enzyme that catalyzes a reversible reaction of interconversion between gamma-aminobutyric acid and a 2-oxoacid to succinate semialdehyde and an L-amino acid. (See Enzyme Commission number 2.6.1.19). In particular, GABA-AT catalyzes a reversible reaction of interconversion between gamma-aminobutyric acid and 2-oxoglutarate to succinate semialdehyde and an L-glutamate. Human GABA-AT alternatively may be referred to as 4-aminobutyrate aminotransferase (ABAT) and is encoded by the ABAT gene located on human chromosome 16, which encodes for a protein that is approximately 56 kDa in size. Human OAT is expressed in liver and kidney but also in the brain. Human OAT is localized in mitochondria. The structure of the human GABA-AT protein has been resolved using X-ray crystallography. (See, e.g., Storici et al. (2018), "Design and Mechanism of (S)-3-Amino-4-(difluoromethylenyl)cyclopent-1-ene-1-carboxylic Acid, a Highly Potent γ-Aminobutyric Acid Aminotransferase Inactivator for the Treatment of Addiction," J. Am. Chem. Soc. 140 (6):2151-2164; the content of which is incorporated herein by reference in its entirety).

As used herein, the term "modulate" means decreasing or inhibiting and/or increasing or augmenting. For example, modulating OAT activity or GABA-AT activity may mean increasing or augmenting OAT activity or GABA-AT, respectively, and/or decreasing or inhibiting OAT activity or GABA-AT, respectively. The therapeutic agents disclosed herein may be administered to a subject in need thereof in order to modulate OAT activity and/or GABA-AT activity, for example in order to inhibit OAT activity and/or GABA-AT activity, where the subject has a disease or disorder associated with OAT activity and/or GABA-AT. Ornithine aminotransferase (OAT) activity may be measured using methods disclosed herein and known in the art. (See, e.g., U.S. Published Application Nos. 2018/0098952, 20160128958, and 2012/0245380; and U.S. Pat. Nos. 8,686,041, and 8,211,865; the contents of which are incorporated herein by reference in their entireties). Gamma-aminobutyric acid-aminotransferase (GABA-AT) activity also may be measured using methods disclosed herein and known in the art. (See, e.g., U.S. Published Application Nos. 2019/0315677, 2019/0256489, 2018/0271816, and 2018/0098952; the contents of which are incorporated herein by reference in their entireties).

The compounds disclosed herein may function as mechanism based enzyme inactivators (MBEI) of OAT and/or GABA-AT. An MBEI is an inert compound that is converted to an active intermediate by an enzyme's normal catalytic machinery. This active intermediate then can form a covalent bond with the enzyme itself or can bind tightly. (See, e.g., Silverman, R. B. "[101 Mechanism-Based Enzyme Inactivators." Methods in enzymology 1995, 249, 240-283; the content of which is incorporate herein by reference in its entirety). Preferably, the disclosed compounds inactivate OAT and/or GABA-AT with a rate of inactivation ($k_{inact}$) of greater than about 0.01 min$^{-1}$, 0.05 min$^{-1}$, 0.1 min$^{-1}$, 0.15 min$^{-1}$, 0.5 min$^{-1}$. 1.0 min$^{-1}$, 5.0 min$^{-1}$, 10 min$^{-1}$, or higher. Preferably, the disclosed compounds inactivate OAT and/or GABA-AT and have an inhibition constant ($K_I$) of less than about 5 mM, 1 mM, 0.5 mM, 0.1 mM, 0.05 mM, 0.01 mM, 0.005 mM, 0.001 mM, or lower.

Subject in Need Thereof

As used herein, a "subject" may be interchangeable with "patient" or "individual" and means an animal, which may be a human or non-human animal, in need of treatment.

As used herein, the term "a subject in need thereof" refers to a human or non-human subject that can be treated with any of the compounds or pharmaceutical compositions disclosed herein when the compounds or pharmaceutical compositions are utilized as therapeutic agents. A subject in need thereof may include a subject having a disease or disorder that is associated with a biological activity of ornithine aminotransferase (OAT). In some embodiments of the disclosed subject matter, a subject in need thereof may include a subject having a disease or disorder that is associated with increased expression of OAT (e.g., a subject having a cancer which overexpresses OAT). A subject in need thereof may include a subject having a disease or disorder that is associated with a biological activity of gamma aminobutyric acid aminotransferase (GABA-AT) and/or concentrations of GABA in the subject.

A subject in need thereof may include a subject having a disease or disorder that is associated with ornithine aminotransferase (OAT), for example a disease or disorder that is associated with expression of OAT (e.g., increased expression of OAT) or a disease or disorder that is associated with a biological activity of OAT (e.g., increased activity of OAT for catalyzing synthesis of glutamate and/or glutamine). Diseases and disorders associated with expression of OAT and diseases or disorders that are associated with a biological activity of OAT are known and may include, but are not limited to cell proliferative diseases or disorders such as cancers.

In some embodiments, a subject in need thereof may include a subject having cancer. A subject in need thereof may include a subject having a cancer selected from, but not limited to, liver cancer (e.g., hepatocellular carcinoma (HCC)), and cancers such as multiple myeloma, leukemia, non-small cell lung cancer, colon cancer, cancer of the central nervous system, melanoma, ovarian cancer, renal cancer, prostate cancer, breast cancer, and pancreatic cancer.

A subject in need thereof may include a subject having a disease or disorder that is associated with gamma aminobutyric acid-amino transferase (GABA-AT) or with concentrations of GABA in the subject. A subject in need thereof may include a subject having a disease or disorder that may be treated by increasing the concentration of gamma aminobutyric acid (GABA) in the subject, for example, via administering to the subject a therapeutic agent that inhibits the activity of GABA-AT, thereby increasing the concentration of GABA in the subject. Diseases and disorders associated with a biological activity of GABA-AT and/or concentrations of GABA in a subject are known and may include, but are not limited to neurological diseases and disorders.

In some embodiments, a subject in need thereof may include a subject having a neurological disease or disorder. In some embodiments, a subject in need thereof is a subject having a disease or disorder selected from Huntington's disease, Alzheimer's disease, and Parkinson's disease.

In some embodiments, a subject in need thereof may include a subject having or at risk for developing an addictive disorder. In some embodiments, a subject in need thereof has or is at risk for developing an addictive disorder selected from cocaine addiction, nicotine addiction, methamphetamine addiction, heroin addiction, and alcohol addiction.

As used herein, a "therapeutic agent" may refer to any agent that is administering to a subject in thereof in order to treat the subject. A therapeutic agent may refer to an agent that modulates the biological activity of OAT, for example where the agent inhibits the biological activity of OAT to catalyze the synthesis of glutamate or glutamine. A therapeutic agent may refer to an agent that modulates the biological activity of GABA-AT, for example where the agent inhibits the biological activity of GABA-AT to degrade GABA to succinic semialdehyde (SSA). Therapeutic agents may include, but are not limited to, small molecules or compounds as disclosed herein. Therapeutic agents may include, but are not limited to, pharmaceutical compositions comprising small molecules or compounds as disclosed herein.

Chemical Entities

Chemical entities and uses for chemical entities are disclosed herein. The chemical entities may be described using terminology known in the art and further discussed below.

As used herein, an asterisk "*" or a plus sign "+" may be used to designate the point of attachment for any radical group or substituent group.

The term "alkyl" as contemplated herein includes a straight-chain or branched alkyl radical in all of its isomeric forms, such as a straight or branched group of 1-12, 1-10, or 1-6 carbon atoms, referred to herein as C1-C12 alkyl, C1-C10-alkyl, and C1-C6-alkyl, respectively.

The term "alkylene" refers to a diradical of an alkyl group (e.g., —(CH$_2$)$_n$— where n is an integer such as an integer between 1 and 20). An exemplary alkylene group is —CH$_2$CH$_2$—.

The term "haloalkyl" refers to an alkyl group that is substituted with at least one halogen. For example, —CH$_2$F, —CHF$_2$, —CF$_3$, —CH$_2$CF$_3$, —CF$_2$CF$_3$, and the like.

The term "heteroalkyl" as used herein refers to an "alkyl" group in which at least one carbon atom has been replaced with a heteroatom (e.g., an O, N, or S atom). One type of heteroalkyl group is an "alkoxy" group.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as C2-C12-alkenyl, C2-C10-alkenyl, and C2-C6-alkenyl, respectively.

The term "alkynyl" as used herein refers to an unsaturated straight or branched hydrocarbon having at least one carbon-carbon triple bond, such as a straight or branched group of 2-12, 2-10, or 2-6 carbon atoms, referred to herein as C2-C12-alkynyl, C2-C10-alkynyl, and C2-C6-alkynyl, respectively.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "C4-8-cycloalkyl," derived from a cycloalkane. Unless specified otherwise, cycloalkyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halo, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the cycloalkyl group is not substituted, i.e., it is unsubstituted.

The term "cycloalkylene" refers to a cycloalkyl group that is unsaturated at one or more ring bonds.

The term "partially unsaturated carbocyclyl" refers to a monovalent cyclic hydrocarbon that contains at least one double bond between ring atoms where at least one ring of the carbocyclyl is not aromatic. The partially unsaturated carbocyclyl may be characterized according to the number oring carbon atoms. For example, the partially unsaturated carbocyclyl may contain 5-14, 5-12, 5-8, or 5-6 ring carbon atoms, and accordingly be referred to as a 5-14, 5-12, 5-8, or 5-6 membered partially unsaturated carbocyclyl, respectively. The partially unsaturated carbocyclyl may be in the form of a monocyclic carbocycle, bicyclic carbocycle, tricyclic carbocycle, bridged carbocycle, spirocyclic carbocycle, or other carbocyclic ring system. Exemplary partially unsaturated carbocyclyl groups include cycloalkenyl groups and bicyclic carbocyclyl groups that are partially unsaturated. Unless specified otherwise, partially unsaturated carbocyclyl groups are optionally substituted at one or more ring positions with, for example, alkanoyl, alkoxy, alkyl, haloalkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl or thiocarbonyl. In certain embodiments, the partially unsaturated carbocyclyl is not substituted, i.e., it is unsubstituted.

The term "aryl" is art-recognized and refers to a carbocyclic aromatic group. Representative aryl groups include phenyl, naphthyl, anthracenyl, and the like. The term "aryl" includes polycyclic ring systems having two or more carbocyclic rings in which two or more carbons are common to two adjoining rings (the rings are "fused rings") wherein at least one of the rings is aromatic and, e.g., the other ring(s) may be cycloalkyls, cycloalkenyls, cycloalkynyls, and/or aryls. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. In certain embodiments, the aromatic ring is substituted at one or more ring positions with halogen, alkyl, hydroxyl, or alkoxyl. In certain other embodiments, the aromatic ring is not substituted, i.e., it is unsubstituted. In certain embodiments, the aryl group is a 6-10 membered ring structure.

The terms "heterocyclyl" and "heterocyclic group" are art-recognized and refer to saturated, partially unsaturated, or aromatic 3- to 10-membered ring structures, alternatively 3- to 7-membered rings, whose ring structures include one to four heteroatoms, such as nitrogen, oxygen, and sulfur. The number of ring atoms in the heterocyclyl group can be specified using 5 Cx-Cx nomenclature where x is an integer specifying the number of ring atoms. For example, a C3-C7 heterocyclyl group refers to a saturated or partially unsaturated 3- to 7-membered ring structure containing one to four heteroatoms, such as nitrogen, oxygen, and sulfur. The designation "C3-C7" indicates that the heterocyclic ring contains a total of from 3 to 7 ring atoms, inclusive of any heteroatoms that occupy a ring atom position.

The terms "amine" and "amino" are art-recognized and refer to both unsubstituted and substituted amines (e.g., mono-substituted amines or di-substituted amines), wherein substituents may include, for example, alkyl, cycloalkyl, heterocyclyl, alkenyl, and aryl.

The terms "alkoxy" or "alkoxyl" are art-recognized and refer to an alkyl group, as defined above, having an oxygen radical attached thereto. Representative alkoxy groups include methoxy, ethoxy, tert-butoxy and the like.

An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, and the like.

The term "carbonyl" as used herein refers to the radical —C(O)—.

The term "oxo" refers to a divalent oxygen atom —O—.

The term "carboxamido" as used herein refers to the radical —C(O)NRR', where R and R' may be the same or different. R and R', for example, may be independently alkyl, aryl, arylalkyl, cycloalkyl, formyl, haloalkyl, heteroaryl, or heterocyclyl.

The term "carboxy" as used herein refers to the radical —COOH or its corresponding salts, e.g. —COONa, etc.

The term "amide" or "amido" or "amidyl" as used herein refers to a radical of the form —$R^1C(O)N(R^2)$—, —$R^1C(O)N(R^2)R^3$—, —$C(O)NR^2R^3$, or —$C(O)NH_2$, wherein R', $R^2$ and $R^3$, for example, are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," or "+" or "-" depending on the configuration of substituents around the stereogenic carbon atom and or the optical rotation observed. The present invention encompasses various stereo isomers of these compounds and mixtures thereof. Stereoisomers include enantiomers and diastereomers. Mixtures of enantiomers or diastereomers may be designated (±)" in nomenclature, but the skilled artisan will recognize that a structure may denote a chiral center implicitly. It is understood that graphical depictions of chemical structures, e.g., generic chemical structures, encompass all stereoisomeric forms of the specified compounds, unless indicated otherwise. Also contemplated herein are compositions comprising, consisting essentially of, or consisting of an enantiopure compound, which composition may comprise, consist essential of, or consist of at least about 50%, 60%, 70%, 80%, 90%, 95%, 96%, 97%, 98%, 99%, or 100% of a single enantiomer of a given compound (e.g., at least about 99% of an S enantiomer of a given compound). The compounds also may have an undefined double stereo bond whose substituents may be present in either of the syn-conformation or the anti-conformation (or alternatively in the E-conformation or the Z-conformation).

The disclosed compounds may exist in protonated forms, deprotonated forms, zwitterionic forms, salts, and hydrates. In some embodiments, the disclosed compounds are provided in a form selected from an acid addition salt, a zwitter ion hydrate, zwitter ion anhydrate, a hydrochloride salt, a hydrobromide salt, or a zwitter ion monohydrate. Acid addition salts include organic acid addition salts and inorganic acid addition salts. Organic acid addition salts include but are not limited to, maleic acid, fumaric acid, benzoic acid, ascorbic acid, succinic acid, oxalic acid, bis-methylenesalicylic acid, methanesulfonic acid, ethane-disulfonic acid, acetic acid, propionic acid, tartaric acid, salicylic acid, citric acid, gluconic acid, lactic acid, malic acid, mandelic acid, cinnamic acid, citraconic acid, aspartic acid, stearic acid, palmitic acid, itaconic acid, glycolic acid, pantothenic acid, p-amino-benzoic acid, glutamic acid, benzene sulfonic acid, and theophylline acetic acid addition salts, as well as the 8-halotheophylline acids, for example 8-bromo-theophylline acid. Inorganic acid addition salts include, but are not limited to, hydrochloric acid, hydrobromic acid, hydroiodic acid, sulfuric acid, sulfamic acid, phosphoric acid, and nitric acid.

The disclosed compounds may be formulated as therapeutic agents for treating a subject in need thereof. In some embodiments, the disclosed compounds may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 µM, 0.005 µM, 0.01 µM, 0.5 µM, 0.1 µM, 1.0 µM, 10 µM, and 100 µM (e.g., 0.1 µM-1.0 µm).

The disclosed compounds and pharmaceutical compositions comprising the disclosed compounds may be administered in methods of treating a subject in need thereof. In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The compounds utilized in the methods disclosed herein may be formulated as a pharmaceutical composition that includes a carrier. For example, the carrier may be selected from the group consisting of proteins, carbohydrates, sugar, talc, magnesium stearate, cellulose, calcium carbonate, and starch-gelatin paste.

The compounds utilized in the methods disclosed herein may be formulated as a pharmaceutical composition that includes one or more binding agents, filling agents, lubricating agents, suspending agents, sweeteners, flavoring agents, preservatives, buffers, wetting agents, disintegrants, and effervescent agents. Filling agents may include lactose monohydrate, lactose anhydrous, and various starches; examples of binding agents are various celluloses and cross-linked polyvinylpyrrolidone, microcrystalline cellulose, such as Avicel® PH101 and Avicel® PH102, microcrystalline cellulose, and silicified microcrystalline cellulose (Pro-Solv SMCC™). Suitable lubricants, including agents that act on the flowability of the powder to be compressed, may include colloidal silicon dioxide, such as Aerosil®200, talc, stearic acid, magnesium stearate, calcium stearate, and silica gel. Examples of sweeteners may include any natural or artificial sweetener, such as sucrose, xylitol, sodium saccharin, cyclamate, aspartame, and acsulfame. Examples of flavoring agents are Magnasweet® (trademark of MAFCO), bubble gum flavor, and fruit flavors, and the like. Examples of preservatives may include potassium sorbate, methylparaben, propylparaben, benzoic acid and its salts, other esters of parahydroxybenzoic acid such as butylparaben, alcohols such as ethyl or benzyl alcohol, phenolic compounds such as phenol, or quaternary compounds such as benzalkonium chloride.

Suitable diluents may include pharmaceutically acceptable inert fillers, such as microcrystalline cellulose, lactose, dibasic calcium phosphate, saccharides, and mixtures of any of the foregoing. Examples of diluents include microcrystalline cellulose, such as Avicel® PH101 and Avicel® PH102; lactose such as lactose monohydrate, lactose anhydrous, and Pharmatose® DCL21; dibasic calcium phosphate such as Emcompress®; mannitol; starch; sorbitol; sucrose; and glucose.

Suitable disintegrants include lightly crosslinked polyvinyl pyrrolidone, corn starch, potato starch, maize starch, and modified starches, croscarmellose sodium, cross-povidone, sodium starch glycolate, and mixtures thereof.

Examples of effervescent agents are effervescent couples such as an organic acid and a carbonate or bicarbonate. Suitable organic acids include, for example, citric, tartaric, malic, fumaric, adipic, succinic, and alginic acids and anhydrides and acid salts. Suitable carbonates and bicarbonates include, for example, sodium carbonate, sodium bicarbonate, potassium carbonate, potassium bicarbonate, magnesium carbonate, sodium glycine carbonate, L-lysine carbonate, and arginine carbonate. Alternatively, only the sodium bicarbonate component of the effervescent couple may be present.

The compounds utilized in the methods disclosed herein may be formulated as a pharmaceutical composition for delivery via any suitable route. For example, the pharmaceutical composition may be administered via oral, intravenous, intramuscular, subcutaneous, topical, and pulmonary route. Examples of pharmaceutical compositions for oral administration include capsules, syrups, concentrates, powders and granules. In some embodiments, the compounds are formulated as a composition for administration orally (e.g., in a solvent such as 5% DMSO in oil such as vegetable oil).

The compounds utilized in the methods disclosed herein may be administered in conventional dosage forms prepared by combining the active ingredient with standard pharmaceutical carriers or diluents according to conventional procedures well known in the art. These procedures may involve mixing, granulating and compressing or dissolving the ingredients as appropriate to the desired preparation.

Pharmaceutical compositions comprising the compounds may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical compositions adapted for transdermal administration may be presented as discrete patches intended to remain in intimate contact with the epidermis of the recipient for a prolonged period of time. For example, the active ingredient may be delivered from the patch by iontophoresis.

Pharmaceutical compositions adapted for topical administration may be formulated as ointments, creams, suspensions, lotions, powders, solutions, pastes, gels, impregnated dressings, sprays, aerosols or oils and may contain appropriate conventional additives such as preservatives, solvents to assist drug penetration and emollients in ointments and creams.

For applications to the eye or other external tissues, for example the mouth and skin, the pharmaceutical compositions are preferably applied as a topical ointment or cream. When formulated in an ointment, the compound may be employed with either a paraffinic or a water-miscible ointment base. Alternatively, the compound may be formulated in a cream with an oil-in-water cream base or a water-in-oil base. Pharmaceutical compositions adapted for topical administration to the eye include eye drops where the active ingredient is dissolved or suspended in a suitable carrier, especially an aqueous solvent.

Pharmaceutical compositions adapted for nasal administration where the carrier is a solid include a coarse powder having a particle size (e.g., in the range 20 to 500 microns) which is administered in the manner in which snuff is taken (i.e., by rapid inhalation through the nasal passage from a container of the powder held close up to the nose). Suitable formulations where the carrier is a liquid, for administration as a nasal spray or as nasal drops, include aqueous or oil solutions of the active ingredient.

Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavoring or coloring agents.

In some embodiments, the pharmaceutical compositions disclosed herein are modified release dosage forms which provide modified release profiles. Modified release profiles may exhibit immediate release, delayed release, or extended release profiles. Conventional (or unmodified) release oral dosage forms such as tablets, capsules, suppositories, syrups, solutions and suspensions typically release medications into the mouth, stomach or intestines as the tablet, capsule shell or suppository dissolves, or, in the case of syrups, solutions and suspensions, when they are swallowed. The pattern of drug release from modified release (MR) dosage forms is deliberately changed from that of a conventional dosage form to achieve a desired therapeutic objective and/or better patient compliance. Types of MR drug products include orally disintegrating dosage forms (ODDFs) which provide immediate release, extended release dosage forms, delayed release dosage forms (e.g., enteric coated), and pulsatile release dosage forms.

An ODDF is a solid dosage form containing a medicinal substance or active ingredient which disintegrates rapidly, usually within a matter of seconds when placed upon the tongue. The disintegration time for ODDFs generally range from one or two seconds to about a minute. ODDFs are designed to disintegrate or dissolve rapidly on contact with saliva. This mode of administration can be beneficial to people who may have problems swallowing tablets whether it be from physical infirmity or psychiatric in nature. Some subjects with an eye disorder may exhibit such behavior. ODDF's can provide rapid delivery of medication to the blood stream through mucosa resulting in a rapid onset of action. Examples of ODDFs include orally disintegrating tablets, capsules and rapidly dissolving films and wafers.

Extended release dosage forms (ERDFs) have extended release profiles and are those that allow a reduction in dosing frequency as compared to that presented by a conventional dosage form, e.g., a solution or unmodified release dosage form. ERDFs provide a sustained duration of action of a drug. Suitable formulations which provide extended release profiles are well-known in the art. For example, coated slow release beads or granules ("beads" and "granules" are used interchangeably herein) in which any of the compounds described herein are applied to beads, e.g., confectioners nonpareil beads, and then coated with conventional release retarding materials such as waxes, enteric coatings and the like. In embodiments, beads can be formed in which any of the compounds described herein are mixed with a material to provide a mass from which the compound leaches out. In embodiments, the beads may be engineered to provide different rates of release by varying characteristics of the coating or mass, e.g., thickness, porosity, using different materials, etc. Beads having different rates of release may be combined into a single dosage form to provide variable or continuous release. The beads can be contained in capsules or compressed into tablets.

ILLUSTRATIVE EMBODIMENTS

The following embodiments are illustrative and should not be interpreted to limit the scope of the claimed subject matter.

Embodiment 1

A compound having the following formula or a protonated form, a deprotonated form, a zwitterionic form, a deuterated form, or a hydrate or a salt thereof:

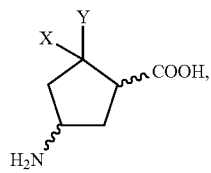

wherein X and Y are independently selected from hydrogen, halo (e.g., difluoro), alkyl, haloalkyl, alkoxy, or X and Y together form alkenyl which optionally is substituted or disubstituted with halo (e.g., where X and Y together form difluoromethenyl), optionally, wherein the compound is (1S,4S)-4-amino-2,2-difluorocyclopentanecarboxylic acid hydrochloride.

Embodiment 2

An enantiomerically pure form of the compound embodiment 1 having the formula:

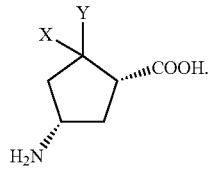

Embodiment 3

The compound of embodiment 1 or 2, wherein X and Y are halo (e.g., fluoro).

Embodiment 4

A composition, optionally a pharmaceutical composition, comprising a compound of the following formula or a protonated form, a deprotonated form, a zwitterionic form, a deuterated form, a hydrate or a salt thereof:

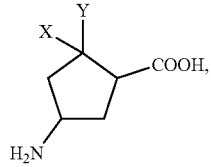

wherein X and Y are independently selected from hydrogen, halo, alkyl, haloalkyl, alkoxy, or X and Y together form alkenyl optionally substituted with halo (e.g., where X and Y together form difluoromethenyl); and wherein at least about 90%, 95%, 96%, 97%, 98%, or 99% of the compound present in the composition has the following stereochemical configuration:

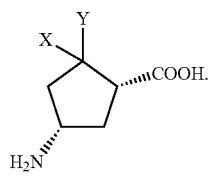

Embodiment 5

The composition of embodiment 4, wherein X and Y are halo (e.g., fluoro).

Embodiment 6

An enantiomerically pure form of the compound embodiment 1 having the formula:

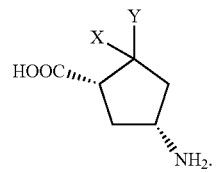

Embodiment 7

The compound of embodiment 6, wherein X and Y are halo (e.g., fluoro).

Embodiment 8

A composition, optionally a pharmaceutical composition, comprising a compound of the following formula or a protonated form, a deprotonated form, a zwitterionic form, a deuterated form, a hydrate or a salt thereof:

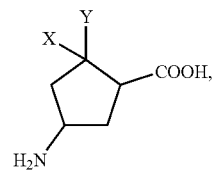

wherein X and Y are independently selected from hydrogen, halo, alkyl, haloalkyl, alkoxy, or X and Y together form alkenyl optionally substituted with halo (e.g., where X and Y together form difluoromethenyl); and
wherein at least about 90%, 95%, 96%, 97%, 98%, or 99% of the compound present in the composition has the following stereochemical configuration:

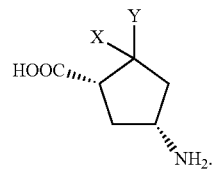

Embodiment 9

The composition of embodiment 8, wherein X and Y are halo (e.g., fluoro).

Embodiment 10

A method for treating a disease or disorder in a subject in need thereof, the method comprising administering to the subject an effective amount of the compound or the composition of any of the foregoing embodiments for treating the disease or disorder.

Embodiment 11

The method of embodiment 10, wherein the disease or disorder is associated with ornithine aminotransferase (OAT) activity.

Embodiment 12

The method of embodiment 10 or 11, wherein the disease or disorder is a cell proliferative disease or disorder such as cancer.

Embodiment 13

The method of embodiment any of embodiments 10-12, wherein the disease or disorder is hepatocellular cancer.

Embodiment 14

The method of embodiment 10, wherein the disease or disorder is associated with γ-aminobutyric acid aminotransferase (GABA-AT) activity.

Embodiment 15

The method of embodiment 10 or 14, wherein the disease or disorder is a neurological disease or disorder.

Embodiment 16

The method of embodiment 10, 14, or 15, wherein the disease or disorder is epilepsy.

Embodiment 17

The method of embodiment 10, 14, or 15, wherein the disease or disorder is Huntington's disease, Alzheimer's disease, or Parkinson's disease.

Embodiment 18

The method of embodiment 10, 14, or 15, wherein the disease or disorder is addiction.

Embodiment 19

The method of embodiment 10, 14, 15, or 18, wherein the disease or disorder is cocaine addiction, nicotine addiction, methamphetamine addiction, heroin addiction, or alcohol addiction.

EXAMPLES

The following examples are illustrative and should not be interpreted to limit the scope of the claimed subject matter.

Example 1 Synthesis of 2-Difluoro Substituted 4-Aminocyclopentanecarboxylic Acids as Inhibitors of Gamma-Aminobutyric Acid Aminotransferase and Human Ornithine Aminotransferase Abstract The GABA-AT inactivator vigabatrin is FDA approved to treat infantile spasms and refractory complex partial seizures. It functions by inhibiting the enzyme γ-aminobutyric acid aminotransferase (GABA-AT), which consequently prevents the breakdown of the inhibitory neurotransmitter γ-aminobutyric acid (GABA). In addition, this inhibition of GABA-AT prevents the production of L-glutamate, an excitatory neurotransmitter. Workarounds to increasing GABA levels, such as using a GABA-AT inactivator instead of directly administering GABA, are necessary because GABA cannot easily cross the blood brain barrier.[1] Vigabatrin has side effects that make the development of new GABA-AT inactivators important. The effective daily dose of vigabatrin is very large, 1-3 g, and partially because of the high dosage, vigabatrin has serious vision-related side effects, especially of the peripheral vision system. The FDA requires a risk management program with vigabatrin to try to prevent long term vision damage such as tunnel vision.[2] For these reasons, the development of other GABA-AT inhibitors is important.

Ornithine aminotransferase (OAT) is another PLP-dependent aminotransferase enzyme that has a similar active site to GABA-AT. Because of the structural similarities, some GABA-AT inhibitors have been found to inhibit OAT as well. OAT has been reported to be overexpressed in hepatocellular carcinoma (HCC), and the inhibition of OAT has been shown to slow tumor growth in rat models.[3] Since HCC is one of the deadliest liver cancers, the development of potent OAT inhibitors is important.

The compound (1S,4S)-4-amino-2,2-difluorocyclopentane-1-carboxylic acid (1) was synthesized and shown to have inhibitory activity against the enzymes GABA-AT and OAT. (See Synthesis Scheme).

Synthesis Scheme for Compound 1 (1S,4S)-4-amino-2,2-difluorocyclopentane-1-carboxylic acid

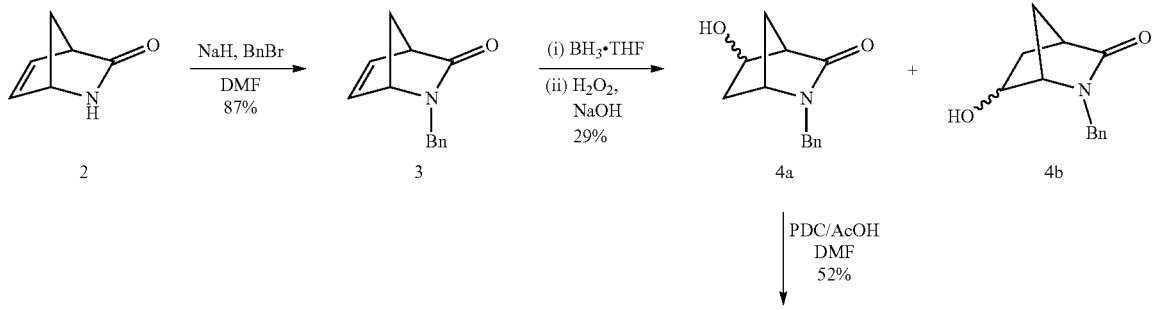

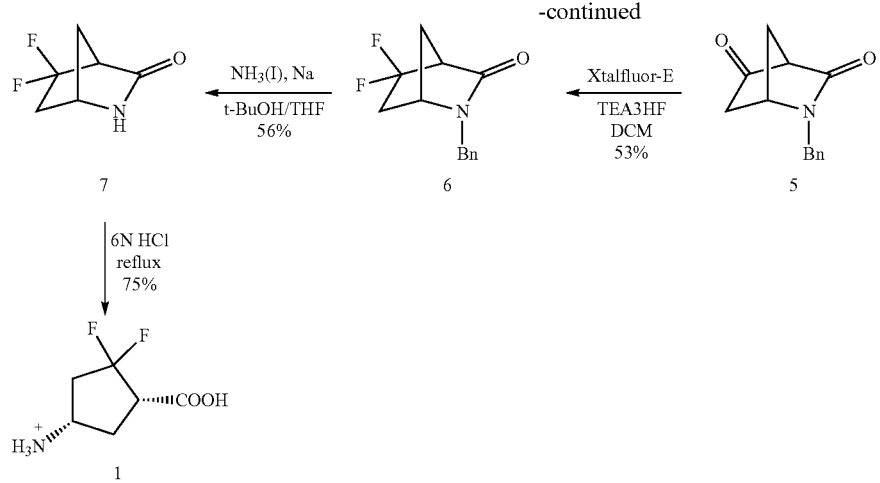

The optically-pure six-step synthesis of 1 was completed from the enantiomerically pure starting material (1S,4R)-2-azabiciclo[2.2.1]hept-5-en-3-one (2). The enantiomerically pure 1 has been shown to inhibit OAT more potently than the racemic version of this compound, implying that this enantiomer is primarily responsible for the racemic compound's inhibition of OAT.

From a variety of cyclopentane-based GABA-AT inhibitors, 1 was designed by adding halogen substituents adjacent to the carboxylic acid group as opposed to the amino group of previously designed inhibitors. The starting material is the commercially-available enantiomerically pure Vince lactam, (1S,4R)-2-azabiciclo[2.2.1]hept-5-en-3-one (2). This lactam's amino group is benzyl protected to produce 3 with benzyl bromide and sodium hydride in DMF. 3 is then hydroborated to produce isomers 4a and 4b using borane tetrahydrofuran at 0° C. Alcohol 4a was then oxidized to a ketone (5) using pyridinium dichromate, and this ketone was difluorinated using Xtalfluor-E to form 6. The benzylamide was deprotected using a Birch reduction, and the lactam opened with hydrochloric acid under reflux to form the desired compound 1.

The enantiomerically pure compound (1) was determined as an inactivator by a concentration-dependent assay with OAT, and it was further assayed in a time-dependent assay to determine $k_{inact}/K_I$, a key parameter to evaluate an irreversible inhibitor of OAT.[4] The ratio of $k_{inact}/K_I$ was determined to be 0.16 min$^{-1}$ mol$^{-1}$ for 1, while it was only 0.052 min$^{-1}$ mol$^{-1}$ for the racemic compound with OAT. In summary, enantiomerically pure 1 was synthesized from an enantiomerically pure Vince lactam in six steps. Enaniomerically-pure compound 1 was shown to selectively inactivate OAT and was more potent than the racemic compound.

Experimental Details (1S,4R)-2-benzyl-2-azabicyclo[2.2.1]hept-5-en-3-one (3)

(1S,4R)-2-azabiciclo[2.2.1]hept-5-en-3-one (2) (1.00 g, 9.16 mmol, 1 equiv) was dissolved in 30 mL anhydrous THF and 30 mL DMF. The solution was cooled to 0° C. while stirring under an argon atmosphere. Sodium hydride (60% dispersion in mineral oil) (671 mg, 16.8 mmol, 1.8 equiv) was added to the solution portion-wise. The resulting solution was stirred at room temperature under an argon atmosphere for 1 h. The reaction was cooled to 0° C. and benzyl bromide (1.3 mL, 11 mmol, 1.2 equiv) was added via a syringe slowly. The resulting solution was stirred at room temperature under argon overnight. 5 mL saturate solution of ammonium chloride was added slowly to quench the reaction. The reaction was poured into 50 mL water and 50 mL ethyl acetate was added. Aqueous layer was extracted with ethyl acetate (3×10 mL). Combined organic layers were separated, washed by 50 mL water, then 50 mL brine, and dried over anhydrous Na$_2$SO$_4$. The solvent was removed under vacuum and the crude product was purified by CombiFlash (Hex/EtOAc 60/40) to give compound 3 as a brown oil (1.581 g, 87%): $^1$H NMR (500 MHz, CDCl$_3$) δ 7.26 (dd, J=8.0, 6.3 Hz, 2H), 7.24-7.19 (m, 1H), 7.16-7.11 (m, 2H), 6.50 (t, J=1.9 Hz, 2H), 4.40 (d, J=14.9 Hz, 1H), 3.98 (p, J=1.9 Hz, 1H), 3.91 (d, J=14.9 Hz, 1H), 3.33 (p, J=1.9 Hz, 1H), 2.24 (dt, J=7.7, 1.8 Hz, 1H), 2.02 (dt, J=7.6, 1.6 Hz, 1H). $^{13}$C NMR (126 MHz, CDCl$_3$) δ 180.0, 139.5, 137.3, 136.5, 128.5 (2C), 128.3 (2C), 127.5, 62.6, 58.3, 53.7, 48.0.

(1S,4R)-2-benzyl-5-hydroxy-2-azabicyclo[2.2.1]heptan-3-one (4a)

Borane tetrahydrofuran (3.93 mL, 3.93 mmol, 2.1 equiv) was added to a round-bottom flask with a stir bar and was kept under an argon atmosphere. The flask was cooled to 0° C., and 3 (373 mg, 1.87 mmol, 1.0 equiv) was added dropwise. The reaction was stirred under argon in an ice bath for 2 h. Hydrogen peroxide (wt 30%, 0.165 mL) and sodium hydroxide (0.46 mL) were very slowly added dropwise to the 0° C. flask, alternating between the hydrogen peroxide and sodium hydroxide. The reaction was allowed to warm to room temperature and to stir in air for 1 h. The reaction was washed with aqueous ammonium chloride (10 mL), extracted with ethyl acetate (3×10 mL), washed with brine, and allowed to dry over sodium sulfate. The crude product was concentrated under vacuum and combined with washed Celite to dry load a C18 reverse phase column. Chromatography (100% water with 0.025% TFA to 100% acetonitrile with 0.01% TFA over 23 min) was used to separate isomers 4a and 4b. The product (4a) was afforded as a clear oil (0.119 g, 29%).]: $^1$H NMR (500 MHz, CDCl$_3$) δ 7.36 (dd, J=8.0, 6.4 Hz, 2H), 7.34-7.29 (m, 1H), 7.28-7.23 (m, 2H), 4.66 (d, J=15.1 Hz, 1H), 4.35-4.21 (m, 1H), 3.90 (d, J=15.0 Hz, 1H), 3.71 (t, J=2.1 Hz, 1H), 2.90 (s, 1H), 2.11-1.88 (m, 3H), 1.56

(dt, J=13.3, 2.5 Hz, 1H). $^{13}$C NMR (126 MHz, CDCl$_3$) δ 176.2, 136.6, 128.7 (2C), 127.9 (2C), 127.6, 70.2, 58.5, 54.8, 44.7, 38.7, 37.1.

(1S,4R)-2-benzyl-2-azabicyclo[2.2.1]heptane-3,5-dione (5)

4a (446 mg, 2.05 mmol, 1 equiv) was dissolved in 6.8 mL DMF. Pyridinium dichromate (2.261 g, 6.16 mmol, 3 equiv) and acetic acid (0.59 mL, 10 mmol, 5 equiv) were added to the solution. The reaction was stirred at room temperature for 5 h and quenched by 3 mL saturate sodium bicarbonate. The mixture was concentrated under vacuum to remove some DMF. Then 10 mL ethyl acetate and 7 mL water were added. Aqueous layer was extracted with ethyl acetate (3×10 mL). Combined organic layers were separated, washed by 25 mL water and 25 mL brine, and then dried over anhydrous Na$_2$SO$_4$. The solvent was removed under vacuum and the crude product was purified by CombiFlash (Hex/EtOAc 40/60) to give 5 as a colorless oil (230 mg, 52%): $^1$H NMR (500 MHz, CDCl$_3$) δ 7.36-7.29 (m, 3H), 7.27-7.23 (m, 2H), 4.66 (d, J=14.9 Hz, 1H), 4.14 (d, J=14.9 Hz, 1H), 4.04 (p, J=2.1 Hz, 1H), 3.28 (d, J=1.9 Hz, 1H), 2.60-2.49 (m, 1H), 2.14-2.08 (m, 2H), 2.01 (dd, J=17.5, 4.4 Hz, 1H). $^{13}$C NMR (126 MHz, CDCl$_3$) δ 206.10, 169.40, 135.69, 128.96 (2C), 128.17 (2C), 128.05, 76.75, 62.11, 56.46, 45.94, 42.19, 39.28.

(1S,4S)-2-benzyl-5,5-difluoro-2-azabicyclo[2.2.1]heptan-3-one (6)

5 (230 mg, 1.07 mmol, 1 equiv) was dissolved in dichloromethane (3.10 mL) in a plastic reaction vessel. Triethylamine trihydrofluoride (0.34 mL, 2.1 mmol, 2 equiv), triethylamine (0.14 mL, 1.1 mmol, 1 equiv) and Xtalfluor-E® (367 mg, 1.6 mmol, 1.5 equiv) were added. The resulting solution was stirred at room temperature for 24 h. The reaction was quenched with 1 mL saturate solution of sodium bicarbonate. Aqueous layer was extracted with dichloromethane (3×5 mL). Combined organic layers were separated, washed with brine, and dried over anhydrous Na$_2$SO$_4$. The solvent was removed under vacuum and the crude product was separated by CombiFlash (Hex/EtOAc 40/60) to give 6 as a pale yellow oil (0.133 g, 53%): $^1$H NMR (500 MHz, CDCl$_3$) δ 7.53-7.28 (m, 3H), 7.28-7.13 (m, 2H), 4.63 (d, J=15.0 Hz, 1H), 4.17 (d, J=15.0 Hz, 1H), 3.77 (q, J=1.9 Hz, 1H), 3.21-2.98 (m, 1H), 2.27-2.15 (m, 1H), 2.11 (dddd, J=16.6, 14.0, 6.9, 3.4 Hz, 1H), 1.99 (dd, J=10.3, 2.9 Hz, 2H); $^{13}$C NMR (126 MHz, CDCl$_3$) δ 171.00 (dd, J=10.5, 2.0 Hz) 135.94, 128.89 (2C), 128.84, 128.73 (dd, J=258.8, 235.2 Hz), 128.20 (2C), 127.98, 56.98 (t, J=4.6 Hz), 54.68 (dd, J=25.7, 22.9 Hz), 45.32, 40.37, 40.34 (t, J=27.2 Hz). $^{19}$F NMR (376 MHz, CDCl$_3$) δ-94.04 (1/2F, m), −94.65 (1/2F, m), −98.62 (1/2F, m), −99.22 (1/2F, m).

(1S,4S)-5,5-difluoro-2-azabicyclo[2.2.1]heptan-3-one (7)

Sodium metal (60 mg, 2.6 mmol, 6.9 equiv) was cut into small pieces and added to a stirred solution of liquid ammonia (1.5 mL) and tertbutyl alcohol (0.26 mL) at −78° C. portionwise under nitrogen flow. A blue solution was formed. Then a solution of 5 (0.090 g, 0.38 mmol) in THF (1 mL) was added slowly to the stirred solution at −78° C. under nitrogen flow. The resulting solution was stirred for 10 min at −78° C., then the reaction was warmed to −30° C. and stirred for 4 min. The reaction was cooled to −78° C. again, and acetic acid (0.26 mL) was added dropwise. The reaction was stirred continuously and slowly warmed to room temperature till liquid ammonia was evaporated. 10 mL ethyl acetate and 10 mL water were added. Aqueous layer was extracted with ethyl acetate (3×10 mL). Combined organic layers were separated, washed with brine, and dried over anhydrous Na$_2$SO$_4$. The solvent was removed under vacuum and the crude product was purified by CombiFlash (DCM/MeOH 90/10) to give 7 as a white solid (0.031 g, 56%): $^1$HNMR (500 MHz, CDCl$_3$) δ 6.91 (br s, 1H), 4.02 (s, 1H), 3.00 (d, J=5.9 Hz, 1H), 2.41-2.03 (m, 4H). $^{13}$C NMR (126 MHz, CDCl$_3$) δ 174.63 (dd, J=10.0, 2.1 Hz), 128.37 (t, J=258.3 Hz), 54.06 (dd, J=25.9, 22.8 Hz), 53.57 (t, J=4.5 Hz), 42.98 (t, J=23.7 Hz), 41.70 (d, J=4.7 Hz).

(1S,4S)-4-amino-2,2-difluorocyclopentanecarboxylic acid hydrochloride (1)

7 (31 mg, 0.21 mmol) was dissolved in 6N HCl (0.8 mL). The resulting solution was stirred under air at 60° C. for 3 h. Water was removed under vacuum and the residue waster was by azeotroping with acetonitrile to give 1 as an off-white powder (32 mg, 75%): $^1$HNMR (500 MHz, D$_2$O) δ 3.95 (p, J=8.0 Hz, 1H), 3.49 (ddd, J=18.3, 14.8, 9.8 Hz, 1H), 2.84 (tdd, J=16.5, 12.3, 9.1 Hz, 1H), 2.62 (dt, J=14.9, 7.9 Hz, 1H), 2.51-2.34 (m, 1H), 2.23 (dt, J=13.7, 9.3 Hz, 1H); $^{13}$C NMR (126 MHz, D$_2$O) δ 171.78, 127.87 (dd, J=256.6, 250.3 Hz), 50.28 (t, J=23.6 Hz), 45.55 (d, J=6.0 Hz), 38.95 (t, J=26.1 Hz), 30.47 (d, J=4.3 Hz). $^{19}$F NMR (376 MHz, D$_2$O) δ-93.85 (1/2F, m), −94.47 (1/2F, m), −96.90 (1/2F, m), −97.52 (1/2F, m).

REFERENCES

1. Silverman, R. B. Design and Mechanism of GABA Aminotransferase Inactivators. Treatments for Epilepsies and Addictions. *Chem. Rev.* 2018. 118, 4037-4070.
2. Postmarket Drug Safety Information for Patients and Providers www.fda.gov/Drugs/DrugSafety/PostmarketDrugSafetyInformationforPatientsandProviders/ucm507990.htm
3. Zigmond, E.; Ya'acov, A. B. et al. Suppression of Hepatocellular Carcinoma by Inhibition of Overexpressed Ornithine Aminotransferase. *ACS Med. Chem. Lett.* 2015. 6, 840-844.
4. Strelow, J. M. A Perspective on the Kinetics of Covalent and Irreversible Inhibition. *SLAS Discovery.* 2017. 22, 3-20.
5. Ilan, Y., Zigmond, E., Silverman, R. B., Lu, H., U.S. Pat. No. 8,211,865 B2 (Aug. 8, 2006), US Grant 8686041B2, Inhibition of ornithine aminotransferase for the treatment of proliferative disorders
6. Juncosa, J. I., K. Takaya, H. V. Le, M. J. Moschitto, P. M. Weerawarna, R. Mascarenhas, D. Liu, S. L. Dewey and R. B. Silverman. "Design and Mechanism of (S)-3-Amino-4-(Difluoromethylenyl)Cyclopent-1-Ene-1-Carboxylic Acid, a Highly Potent Gamma-Aminobutyric Acid Aminotransferase Inactivator for the Treatment of Addiction." *J Am Chem Soc* 2018, 140, 2151-2164. PMC5812813.
7. Silverman, R. B.; Takaya, K.; Le, H. V.; Juncosa, J. I. U.S. Pat. No. 9,670,141 B2 (Jun. 6, 2017). (S)-3-Amino-4-(difluoromethylenyl)cyclopent-1-ene-1-carboxylic acid, and related compounds as GABA aminotransferase inactivators for the treatment of epilepsy, addiction and hepatocellular carcinoma
8. U.S. Published Application Nos. 20190359555; 20190315677; 20180271816; 20180098952, 20170239202; 20170101364; 20150196522; 20160128958; and 20130041028; the contents of which are incorporated herein by reference.

Example 2—Synthesis of Optically-Pure GABA-AT and OAT Inactivators

Abstract

Both enantiomers of an optically-pure cyclopentane-based GABA-AT and OAT inactivator were synthesized and characterized. The racemic version of this compound was previously synthesized and found to inactivate GABA-AT. It was hypothesized that the optically-pure compound would result in greater inactivation, so the inactivation of these two enantiomers were directly compared for GABA-AT and OAT. The S, S enantiomer was found to inactivate OAT, but only very weakly inhibit GABA-AT. The R, R enantiomer did not inhibit either OAT or GABA-AT potently. In addition, studying the mechanism of the compound's inhibition of the enzyme may be valuable because of the novel location of the fluorine substituents on the cyclopentane ring. The synthesis of a deuterated compound has been started in order to determine if a specific proton is removed in the rate determining step of inactivation of OAT.

INTRODUCTION

Infantile spasms is a seizure disorder that is diagnosed in around 1,200 infants in the US every year. The symptoms of this disorder are spasms that vary from small head bobs to full body spasms. The prognosis for diagnosed infants is very poor because only 24% of diagnosed children have a favorable long-term outcome. Successful treatment of the spasms is important because it typically leads to improved future outcomes.[1]

Vigabatrin is a γ-aminobutyric acid aminotransferase (GABA-AT) inactivator that has been approved by the FDA to treat infantile spasms. It functions by inhibiting the enzyme GABA-AT, which consequently prevents the breakdown of the inhibitory neurotransmitter γ-aminobutyric acid (GABA). In addition, this inhibition of GABA-AT prevents the production of L-glutamate, an excitatory neurotransmitter. Workarounds to increasing GABA levels, such as using a GABA-AT inactivator instead of directly administering GABA, are necessary because GABA cannot easily cross the blood brain barrier.[2]]

Vigabatrin has issues which make the development of new GABA-AT inactivators important. The effective dose of vigabatrin is very large, 1-3 g. Partially due to the high dosage, vigabatrin has serious vision-related side effects, especially of the peripheral vision system. The FDA requires a risk management program with vigabatrin to try to prevent long term vision damage such as tunnel vision.[3]

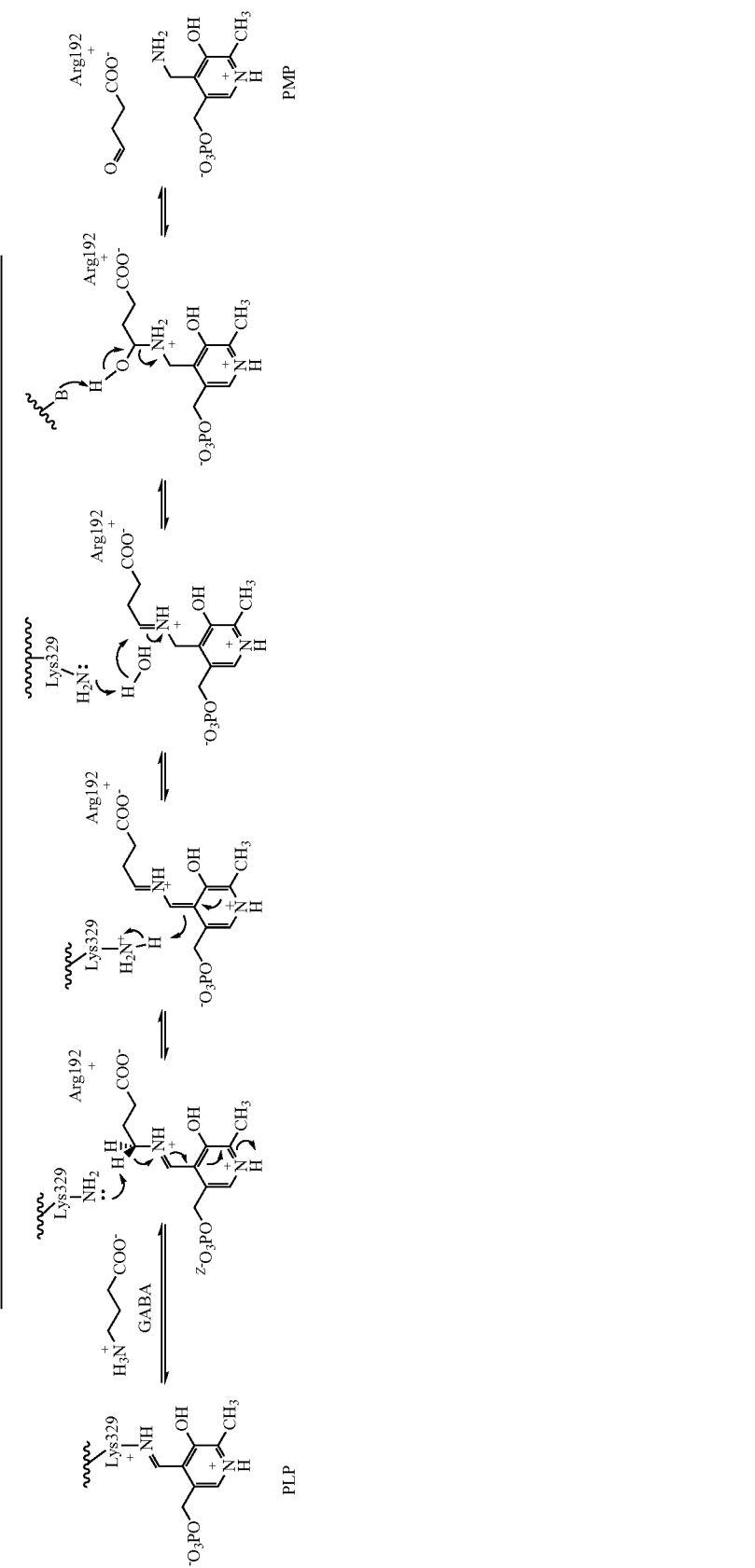
Scheme 1. Mechanism of the Breakdown of GABA to SSA (from Silverman, R. B. Design and Mechanism of GABA Aminotransferase Inactivators. Treatments for Epilepsies and Addictions. Chem. Rev. 2018, 118, 4037-4070).

In addition to treating infantile spasms, GABA-AT inactivators including vigabatrin and CPP-115 (8) may be useful in treating substance addiction. The use of drugs such as nicotine, cocaine, and heroin lead to an increase of dopamine in the nucleus accumbens in the brain, but GABA downregulates this dopamine release. As a result of this, GABA-AT inactivators have been shown to be able to treat a variety of substance addictions in various animal tests.[4]

Vigabatrin functions mechanistically by blocking the PLP dependent breakdown of GABA to succinic semialdehyde. The vigabatrin covalently bonds to the amino group of Lys329 in GABA-AT. This bond prevents the interaction between Lys329 and GABA, which prevents the breakdown of GABA to succinic semialdehyde (SSA) by GABA-AT. Therefore, GABA levels increase in the brain as less is being broken down.[2]

Ornithine aminotransferase (OAT) is another PLP-dependent aminotransferase enzyme that has a similar active site to GABA-AT. Due to the similarities, some GABA-AT inhibitors have been found to inhibit OAT as well. OAT has been reported to be overexpressed in hepatocellular carcinoma (HCC), and the inhibition of OAT has been shown to slow tumor growth in rat models. Since HCC is one of the deadliest liver cancers, the development of potent OAT inhibitors is important.[5]

The target compound, NAL-1-47, has a unique placement of the halogen substituents on the cyclopentane ring that makes it unique from previously tested cyclopentane-based and cyclopentene-based GABA-AT and OAT inhibitors. This novel location of the halogen substituents may change the mechanism in which the compound interacts with GABA-AT and OAT. Understanding the mechanism of the interaction of NAL-1-47 with GABA-AT and OAT may be useful in the design of future inhibitors.

Results and Discussion

The starting material for the synthesis of NAL-1-47 is the commercial compound (1S)-(+)-2-azabiciclo[2.2.1]hept-5-en-3-one (11).

Scheme 2. Synthetic route of NAL-1-47.

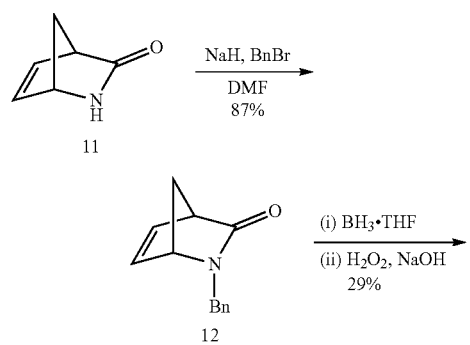

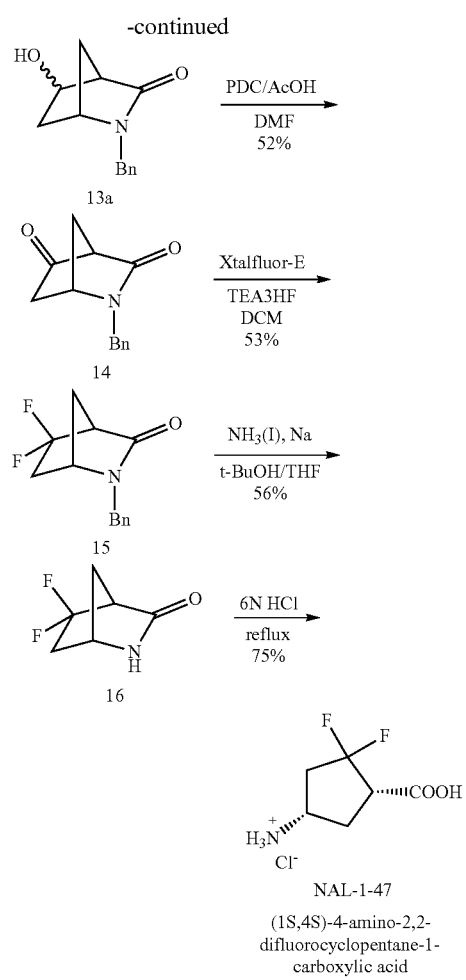

The benzyl protecting group was chosen because previous lab members were unable to deprotect the PMB protected amide. The benzyl protection reaction created a small amount of polymer, but the yield was still good. In addition, increasing the ratio of DMF in the solvent mixture was found to increase yields slightly. Hydroboration to form isomer 13a initially failed due to using too high of a concentration of NaOH which led to a very low yield. Eventually, using the established procedure of borane DMS and then hydrogen peroxide and sodium hydroxide was successful with acceptable yields. The use of other borane reagents was attempted (Table 1).

TABLE 1

| Isomer ratio for various reaction conditions | | |
|---|---|---|
| Borane Reagent | Temperature | Result |
| Borane DMS | R.T. | About 1:1 isomer ratio |
| Borane THF | R.T. | Good ratio; significant amount of byproduct formed |
| Borane THF | 0° C. | About 2:1 isomer ratio |
| Borane THF | −12° C. | About 1.4:1 isomer ratio |
| 9-BBN | R.T. | No reaction |
| 9-BBN | 40° C. | No reaction |

The ratio between the two produced isomers was improved, especially by changing the temperature. The conditions that most improved the ratio between isomers, however, also produced a larger amount of byproduct, and this byproduct reduced the yield's improvement to an almost insignificant improvement. The ratio of isomers was confirmed using LCMS and NMR. The borane THF at 0° C. was overall the best yield, but only was marginally better than the standard borane DMS at room temperature. The separation of the two isomers originally failed with C18 reverse phase chromatography because of the use of liquid loading with the product mixture dissolved in acetonitrile. Dry loading the column with the product in washed Celite separated the two isomers.

The oxidation of the alcohol 13a to form the ketone intermediate 14 lost significant product in the extraction, possibly due to solvation in the aqueous layer. Evaporating DMF under vacuum prior to the extraction improved the yield from 23% to 52%. The difluorination reaction successfully produced product, but there was incomplete conversion possibly caused by the decomposition of the fluorinating reagent. Using a plastic reaction vessel instead of the borosilicate glass reaction vessel led to full conversion and a yield of 53%. It was hypothesized that using hydrobromic acid at reflux would be able to afford NAL-1-47 directly from 15 by deprotecting the benzyl group and hydrolyzing the amide in one step. This reaction was not successful; the amide was opened, but the benzyl protecting group remained. A Birch reduction did successfully remove the benzyl group (16) with a 56% yield followed by acidic hydrolysis of the amide using 6N hydrochloric acid to afford the targeted compound NAL-1-47 with a 75% yield. The final compound was purified using reverse phase chromatography to obtain 32 mg of NAL-1-47, and its structure was confirmed by NMR.]

Figure 3:
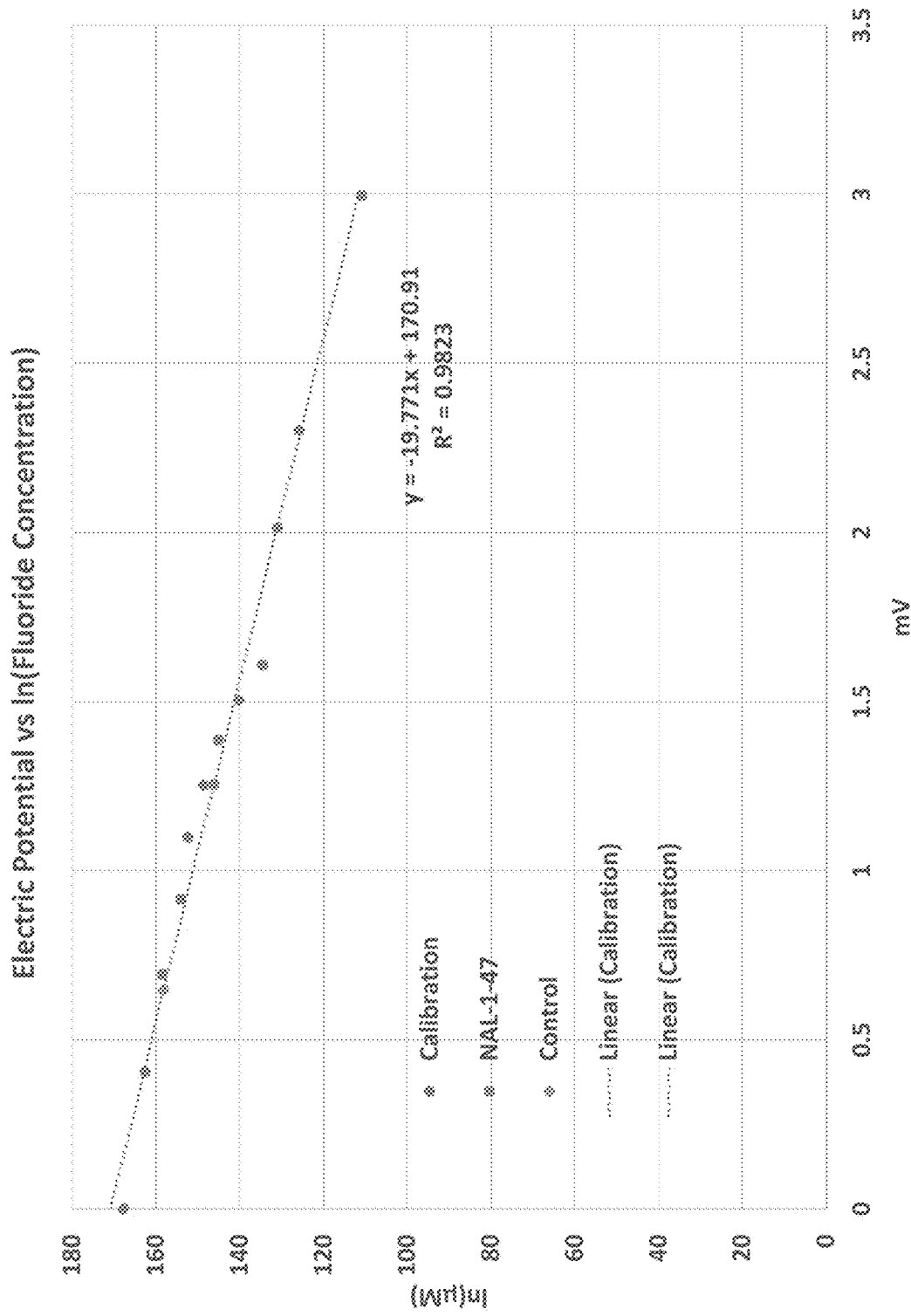
FIG. 3. OAT Fluoride Release Assay with NAL-1-47.

NAL-1-47 was assayed with OAT and was shown to inactivate OAT, while NAL-1-47 does not inhibit GABA-AT potently. An OAT fluoride release assay was performed with NAL-1-47 and it was calculated that there were 13.02 fluoride ions released per enzyme active site (FIG. 3). This high amount of fluoride release in the assay without α-ketoglutarate, which is necessary to regenerate pyridoxal 5'-phosphate (PLP), implies that there is a mechanistic pathway that releases fluoride, without modification of PLP, and does not inhibit the enzyme.

Intact protein mass spectrometry was performed for OAT and NAL-1-47, which showed that the main adduct had a mass of 354.8 Da (Data not shown), and this mass corresponds to the adduct of the hypothesized mechanism (Scheme 3).

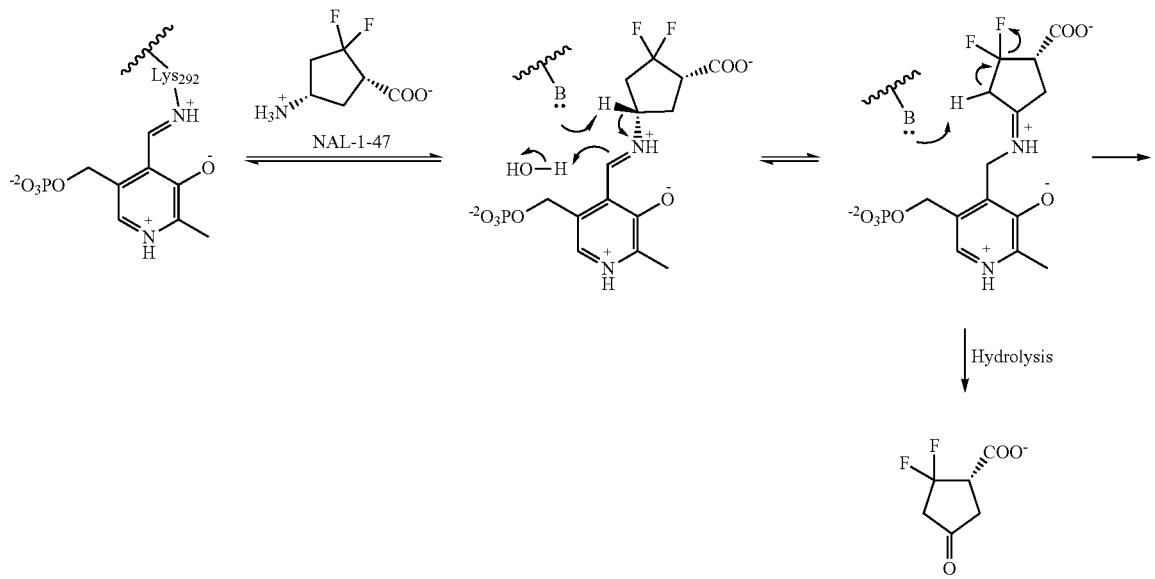

Scheme 3. Proposed Mechanism of Inactivation of OAT by NAL-1-47

-continued

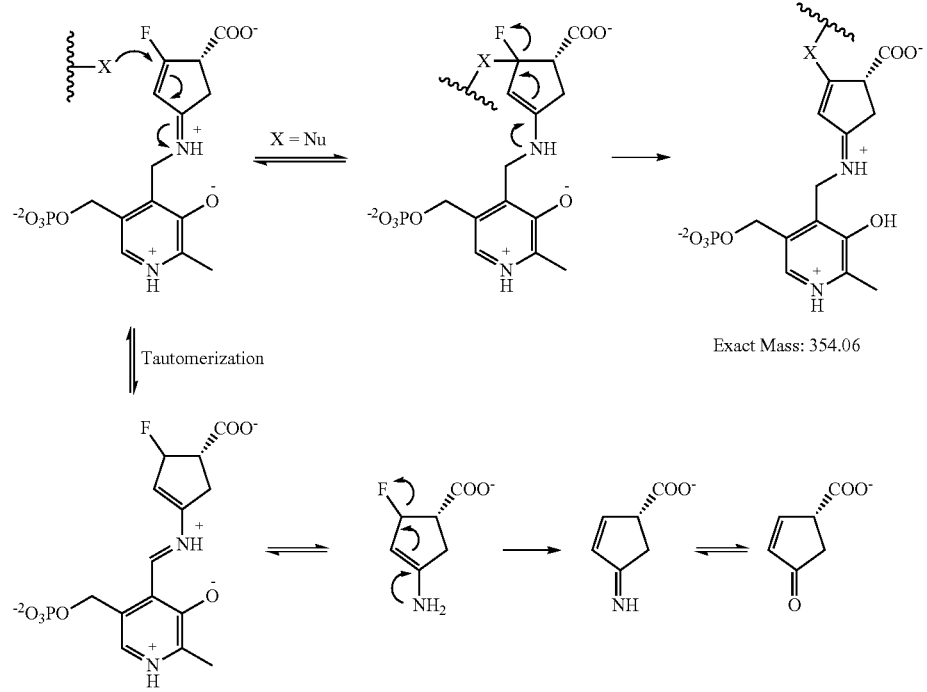

NAL-1-47 was incubated with OAT then dialyzed to determine whether it functions as a reversible inhibitor or an irreversible inactivator of OAT. NAL-1-47 was pre-incubated overnight at 37° C. with OAT. The remaining activity of the OAT was determined for 20, 50, 80, and 120 equiv of NAL-1-47 per OAT active site. The inactivated OAT was then dialyzed for 144 h and using a control, it was confirmed that the control OAT retained the majority of its activity after this dialysis. After this dialysis, the inhibited OAT did not regain any activity, which suggests that NAL-1-47 is an irreversible inactivator of OAT (Table 2).

TABLE 2

Dialysis Assay of NAL-1-47 with OAT

| Percent Activity Remaining of OAT with NAL-1-47 (%) | Percent Activity Remaining of OAT with NAL-1-47 after 144 h Dialysis (%) |
|---|---|
| 20 equiv | 67.3 | 63.3 |
| 50 equiv | 52.5 | 38.5 |
| 80 equiv | 31.7 | 27.6 |
| 120 equiv | 21.1 | 15.1 |

A possible mechanism for the inactivation of OAT by NAL-1-47 has been proposed based on the mass of the adduct found using intact protein mass spectrometry and the inactivation mechanisms of similar compounds with OAT (Scheme 3).

The proposed mechanism is a Michael addition mechanism with an unknown nucleophilic residue in the active site. The proposed mechanism includes a pathway for the release of fluoride ions through a tautomerization pathway, and in this pathway, PLP is not modified. The PLP must not be modified in this pathway because the fluoride release assay was done without α-ketoglutarate and all excess PLP was dialyzed out. The high partition ratio through a hydrolysis pathway is also included in the proposed mechanism.

In this pathway, PLP is transformed into PMP, and this is possible because the partition assay was performed with α-KG. Metabolomics, crystallography, and computer modelling are planned in order to further understand the mechanism of inactivation.

To directly compare the inactivation of NAL-1-47 with OAT and GABA-AT to the other enantiomer, the other enantiomer, NAL-1-73, was synthesized (Scheme 4).

Scheme 4. Synthetic Route of 23

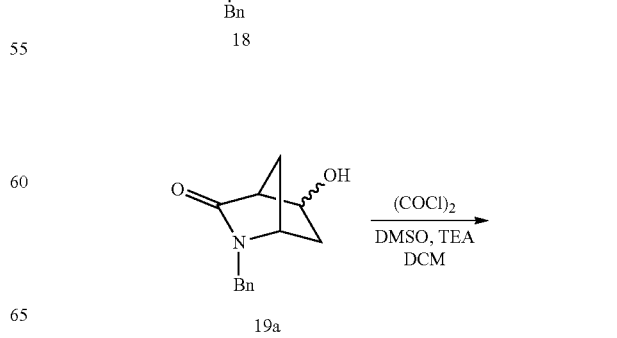

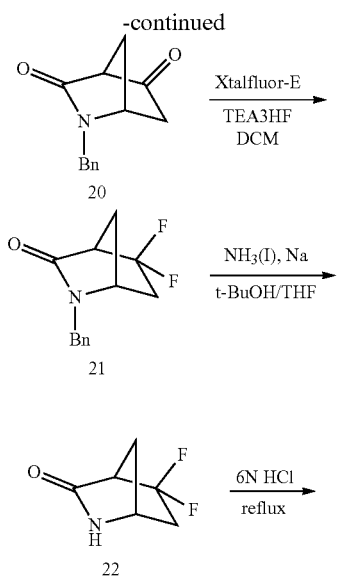

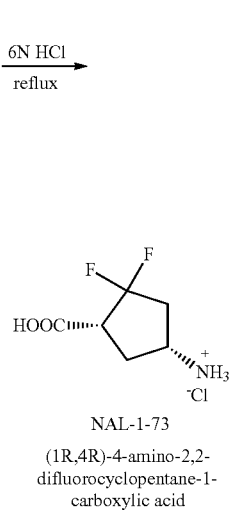

NAL-1-73
(1R,4R)-4-amino-2,2-difluorocyclopentane-1-carboxylic acid

The synthesis of NAL-1-73 is very similar to the synthesis of NAL-1-47, but starts with (1R)-(−)-2-azabiciclo[2.2.1]hept-5-en-3-one (17), and a different oxidation was used to oxidize the alcohol to a ketone. The hydroboration oxidation to produce the isomers 19a and 19b successfully produced these isomers in a favorable ratio, but the separation of these two isomers was problematic due to the column having too high of a pressure at normal flow rates, so a very low flow rate had to be used. This problem was probably due to an old C18 column being used, and this low flow rate led to poor separation of the isomers due to diffusion in the column. Some 19a was still successfully separated, but this issue still led to a yield of only 17%. A Swern oxidation instead of a PCC oxidation was used to produce 20 in an attempt to achieve higher yields since the PCC oxidation was low yielding when producing 14. The Swern oxidation cleanly produced 20 with acceptable yields. The synthesis was then completed using the same procedure as the synthesis of NAL-1-47, and NAL-1-73 was successfully produced as a white powder.

Previously, the racemic compound's assay data from a previous group member suggested that the racemic compound inhibited GABA-AT more potently than NAL-1-47, so it was hypothesized NAL-1-73 was responsible for the racemic compound's inhibitory activity. When NAL-1-73 was successfully synthesized, both NAL-1-47 and NAL-1-73 were assayed with GABA-AT in a concentration dependent assay, and it was found that neither compound potently inhibited GABA-AT (Table 3).

TABLE 3

Concentration dependent assay of GABA-AT with NAL-1-47/73

| Conc. (mM) | NAL-1-47 Activity Remaining (%) | NAL-1-73 Activity Remaining (%) |
|---|---|---|
| 10 | 44.7 | 55.3 |
| 5 | 67.8 | 70.3 |
| 2.5 | 88.3 | 85.2 |
| 1.25 | 93.4 | 88.8 |
| 0.625 | 93.6 | 103.5 |
| 0.3125 | 91.0 | 95.1 |
| 0.1563 | 100.7 | 94.5 |
| 0.0781 | 110.6 | 100.9 |

Figure 4:
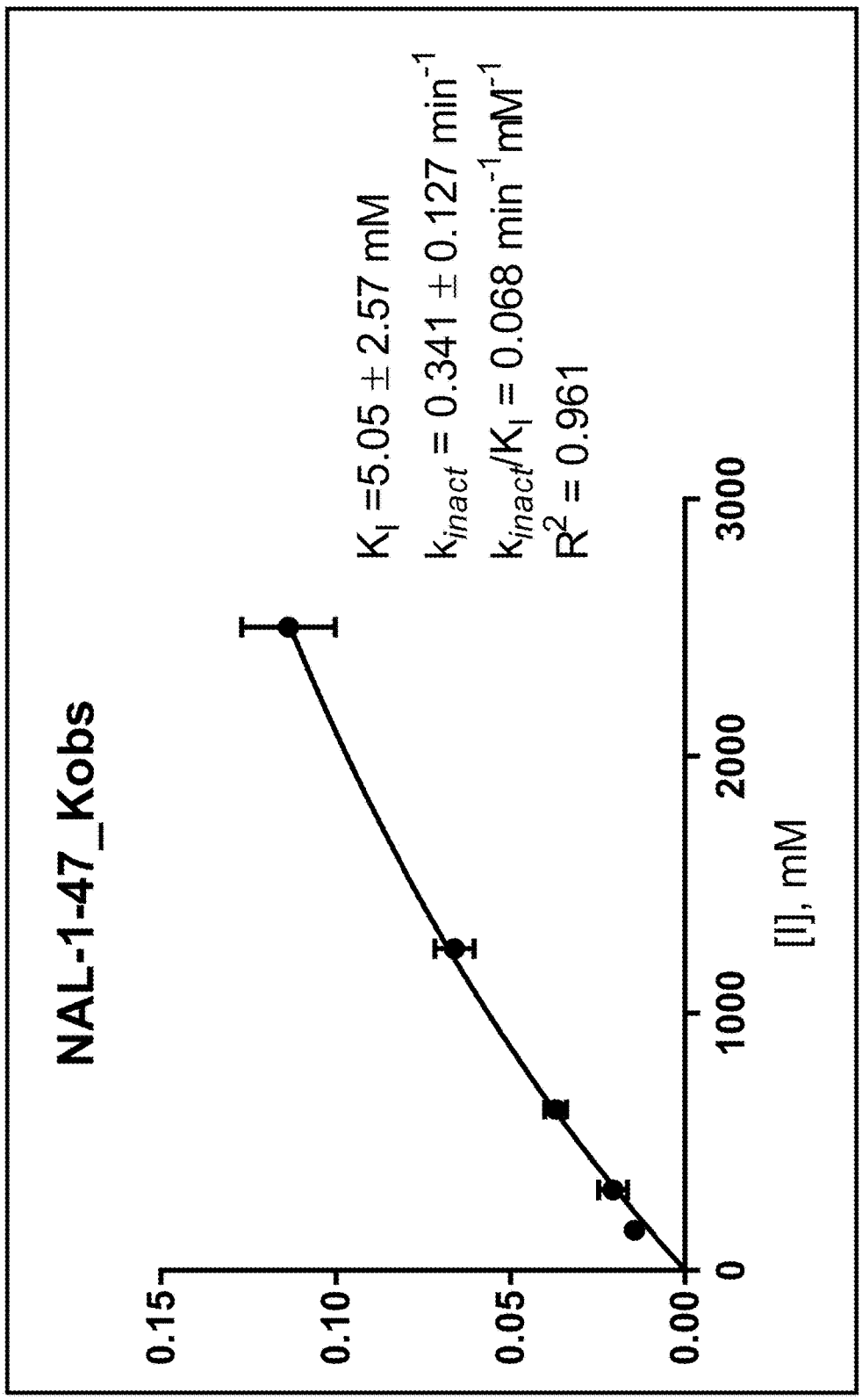
FIG. 4. Time-dependent Assay of NAL-1-47 with OAT.

In addition, both compounds were assayed with GABA-AT in time-dependent assays, but no significant inhibitory activity was found. This suggests that the previous data for the racemic compound was inaccurate. NAL-1-47 and NAL-1-73 were also assayed with OAT, and NAL-1-47 was found to inhibit OAT potently while NAL-1-73 was not. For NAL-1-47, the ratio of $k_{inact}/K_I$, a key parameter to evaluate an irreversible inhibitor,[6] was determined to be 0.068 min$^{-1}$ mM$^{-1}$ (FIG. 4).

Figure 5:
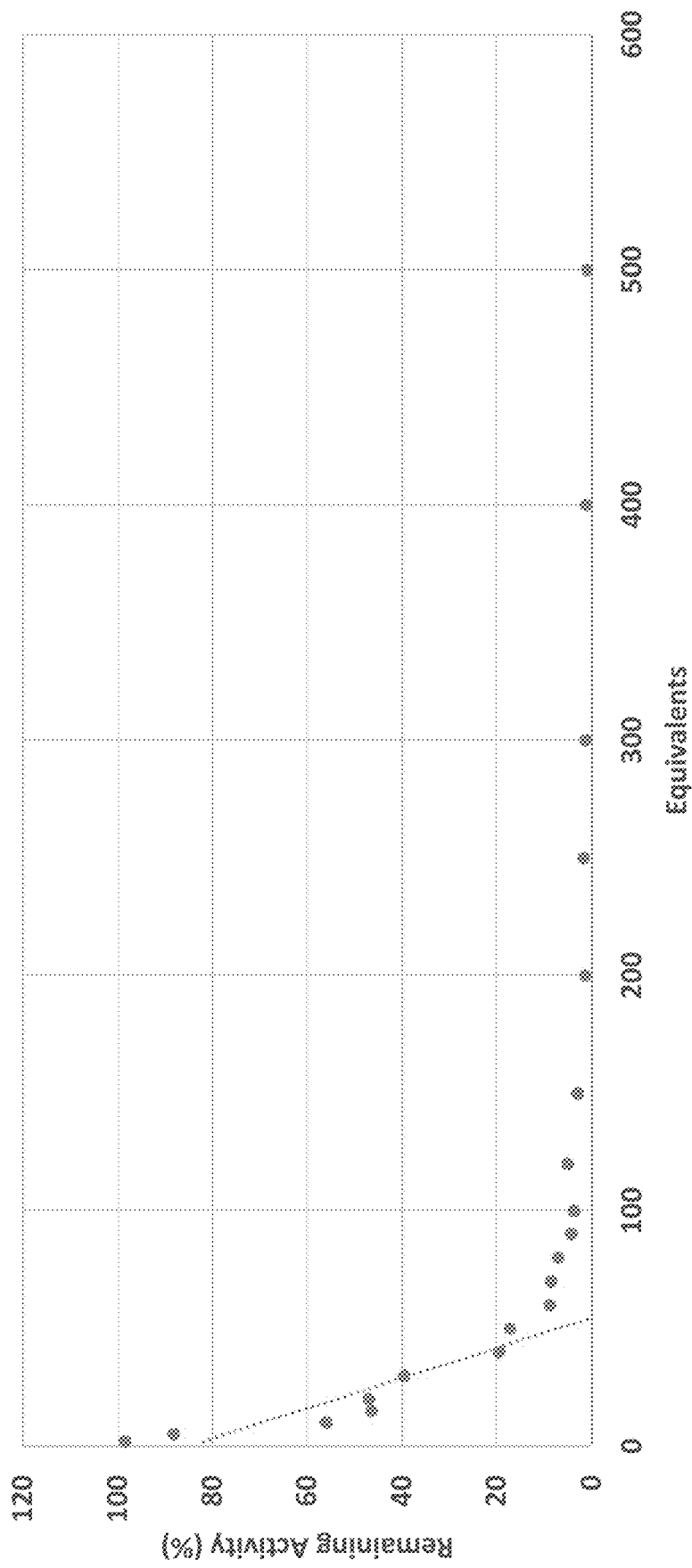
FIG. 5. Partition Assay of NAL-1-47 with OAT.

A partition ratio assay of OAT with NAL-1-47 was performed to determine the ratio of the compound acting as a substrate to the compound inactivating the enzyme. Due to variations in the range of equivalents used, previous partition ratio assays of NAL-1-47 with OAT resulted in a large variation in the calculated partition ratio, so a large amount of data points was used. The partition ratio was found to be 54.5 (FIG. 5).

In order to determine whether the proposed inactivation mechanism of OAT by NAL-1-47 is accurate, a deuterated compound, (1S,4S)-4-amino-3,3-dideutero-2,2-difluorocyclopentane-1-carboxylic acid is being synthesized (Scheme 5).

Scheme 5. Synthetic Route of 30

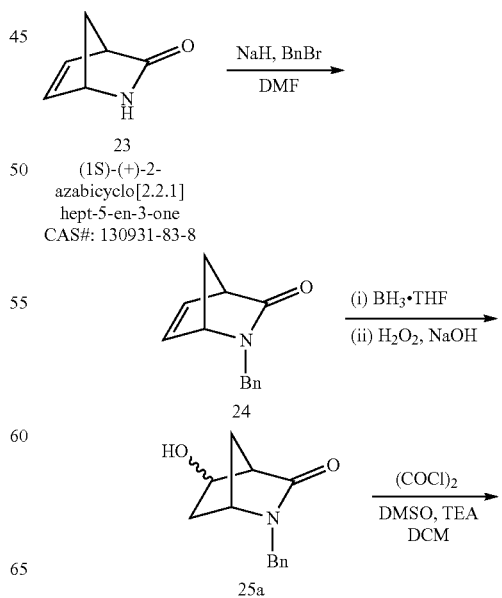

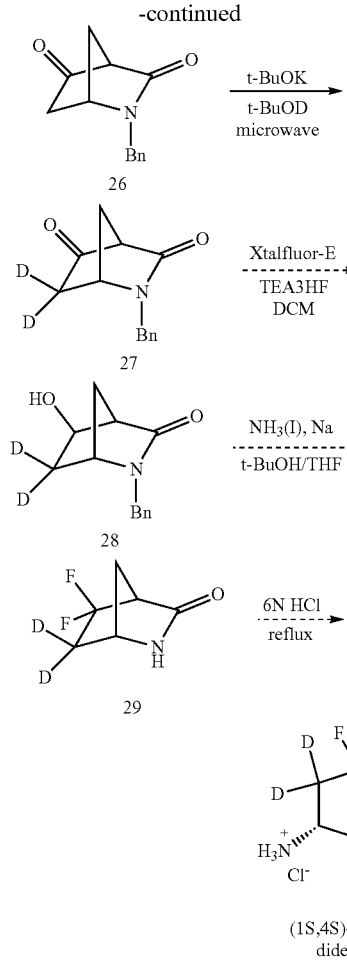

26

27

28

29

30
(1S,4S)-4-amino-3,3-
dideutero-2,2-
difluorocyclopentane-1-
carboxylic acid

After synthesizing this compound, it will be assayed with OAT. If the rate determining step of the proposed inactivation mechanism is the deprotonation of the deuterated position as hypothesized, a reduction in rate should be observed due to the kinetic isotope effect. The synthesis of this deuterated compound follows the synthetic route of NAL-1-47 with a deuteration step between the oxidation step and the difluorination step. The key deuteration step has been successfully completed using t-BuOK as a base and t-BuOD as a proton source and solvent. This reaction was performed under a dry argon atmosphere in a microwave. A variety of other conditions was attempted before this deuteration was successfully completed, and these previously attempted conditions probably failed due to the nucleophilicity of the solvents, which led to the opening of the amide (Table 4).

Experimental Details

All reactions except the preparation of 13a, 15, 20, and 27 were done by Chengming He's previous racemic synthesis. The preparation of 13a and 15 were only slightly varied from Chengming's synthesis.

Preparation of 13a

Borane tetrahydrofuran (3.93 mL, 3.93 mmol, 2.1 equiv) was added to a round-bottom flask with a stir bar and was kept under an argon atmosphere. The flask was cooled to 0° C., and 12 (373 mg, 1.87 mmol, 1.0 equiv) was added dropwise. The reaction was stirred under argon in an ice bath for 2 h. Hydrogen peroxide (0.165 mL) and sodium hydroxide (0.46 mL) were very slowly added dropwise to the 0° C. flask, alternating between the hydrogen peroxide and sodium hydroxide. The reaction was allowed to warm to room temperature and to stir in air for 1 h. The reaction was washed with aqueous ammonium chloride (10 mL), extracted with ethyl acetate (3×10 mL), washed with brine, and allowed to dry over sodium sulfate. The crude product was concentrated under vacuum and combined with washed Celite to dry load a C18 reverse phase column. Chromatography (100% water with 0.025% TFA to 100% acetonitrile with 0.01% TFA over 23 min). The product (13a) was afforded as a clear oil (0.119 g, 29%).

Preparation of 15

Same as established procedure except no additional reagents were added after 24 hours, and a plastic reaction vessel was used for the reaction.

Preparation of 20

Dichloromethane (11 mL) was added to a round-bottom flask with a stir bar at −78° C. under an argon atmosphere. Oxalyl chloride (0.290 mL, 3.38 mmol, 1.4 equiv) was added to the flask. Dimethyl sulfoxide (0.395 mL, 5.56 mmol, 2.3 equiv) was then added dropwise, and the reaction was stirred for 10 min at −78° C. Next, 19 (525 mg, 2.42 mmol, 1.0 equiv) was dissolved in dichloromethane (11 mL), and this solution was added to the reaction flask and allowed to stir for 10 min. Triethylamine (2.36 mL, 16.9 mmol, 7.0 equiv) was added to the flask, and the reaction was allowed to stir for 10 min. The reaction was allowed to warm to room temperature, and saturated ammonium chloride solution (10 mL) was added to quench the reaction. The reaction was extracted with dichloromethane (3×10 mL), concentrated under vacuum, washed with brine, and allowed to dry over sodium sulfate.

Preparation of 27

A stir bar, 26 (10 mg, 0.046 mmol, 1.0 equiv), and tert-butoxide (7.8 mg, 0.070 mmol, 1.5 equiv) was added to

TABLE 4

Deuteration Conditions and Results

| Base | Solvent | Conditions | Result |
|---|---|---|---|
| $K_2CO_3$ | MeOD | 60° C., overnight | Amide opened, deuteration |
| $K_2CO_3$ | $D_2O$/Acetone-d6 | 60° C., overnight | Amide opened, no deuteration |
| $K_2CO_3$ | tert-Butanol-OD | 60° C., overnight | Amide opened, no deuteration |
| t-BuOK | tert-Butanol-OD | 60° C., overnight | No reaction |
| t-BuOK | tert-Butanol-OD | μwave, 100° C., 1 hour | No reaction |
| t-BuOK | tert-Butanol-OD | μwave, 150° C., 1 hour | Desired deuterated product formed | a microwave vial under a dry argon atmosphere. Tert-butanol-OD (0.60 mL) was added to the same vial. The microwave vial was sealed, and the reaction mixture was allowed to react under microwave conditions at 150° C. for 1 h.

REFERENCES

1. Infantile Spasms www.childneurologyfoundation.org/disorders/infantile-spasms/
2. Silverman, R. B. Design and Mechanism of GABA Aminotransferase Inactivators. Treatments for Epilepsies and Addictions. *Chem. Rev.* 2018. 118, 4037-4070.
3. Postmarket Drug Safety Information for Patients and Providers http://www.fda.gov/Drugs/DrugSafety/PostmarketDrugSafetyInformationforPatientandProv iders/ucm507990.htm
4. Pan, Y.; Gerasimov, M. R. et al. (1S,3S)-3-Amino-4-difluoromethylenyl-1-cyclopentanoic Acid (CPP-115), a Potent γ-Aminobutyric Acid Aminotransferase Inactivator for the Treatment of Cocaine Addiction. *J. Med. Chem.* 2012. 55, 357-366.
5. Zigmond, E.; Ya'acov, A. B. et al. Suppression of Hepatocellular Carcinoma by Inhibition of Overexpressed Ornithine Aminotransferase. *ACS Med. Chem. Lett.* 2015. 6, 840-844.
6. Strelow, J. M. A Perspective on the Kinetics of Covalent and Irreversible Inhibition. *SLAS Discovery.* 2017. 22, 3-20.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

I claim:

1. An enantiomerically pure form of a compound having the following formula, or a protonated form, a deprotonated form, a zwitterionic form, a deuterated form, or a hydrate or a salt thereof:

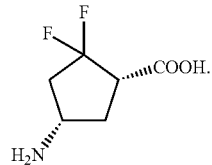

2. A pharmaceutical composition comprising the compound of claim 1.

3. A method for treating a disease or disorder in a subject in need thereof, the method comprising administering to the subject an effective amount of the compound of claim 1 or a pharmaceutically composition comprising an effective amount thereof.

4. The method of claim 3, wherein the disease or disorder is associated with ornithine aminotransferase (OAT) activity.

5. The method of claim 3, wherein the disease or disorder is hepatocellular cancer.

6. A method for inhibiting activity of ornithine aminotransferase (OAT), the method comprising contacting the OAT with the compound of claim 1.

7. The method of claim 6, wherein the OAT is present within a cell.

* * * * *